United States Patent
Kim et al.

(10) Patent No.: US 11,659,756 B2
(45) Date of Patent: *May 23, 2023

(54) SENSOR UNIT, DISPLAY DEVICE INCLUDING THE SAME, AND METHOD FOR MEASURING MOISTURE USING THE SAME

(71) Applicant: Samsung Display Co., Ltd., Yongin-si (KR)

(72) Inventors: Yu Na Kim, Seoul (KR); Soo Jung Lee, Suwon-si (KR); Keum Dong Jung, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/520,706

(22) Filed: Nov. 7, 2021

(65) Prior Publication Data

US 2022/0102435 A1    Mar. 31, 2022

Related U.S. Application Data

(63) Continuation of application No. 16/913,666, filed on Jun. 26, 2020, now Pat. No. 11,171,185.

(30) Foreign Application Priority Data

Aug. 9, 2019    (KR) .......................... 10-2019-0097397

(51) Int. Cl.
*H01L 27/32*    (2006.01)
*G06F 3/044*    (2006.01)
(Continued)

(52) U.S. Cl.
CPC ............ *H01L 27/323* (2013.01); *A61B 5/441* (2013.01); *G06F 3/0412* (2013.01);
(Continued)

(58) Field of Classification Search
CPC ....... A61B 5/441; A61B 5/443; A61B 5/6898; A61B 2560/0252; A61B 2562/0214;
(Continued)

(56) References Cited

U.S. PATENT DOCUMENTS

2006/0281981 A1    12/2006    Jang et al.
2016/0274726 A1     9/2016    Chung et al.
(Continued)

FOREIGN PATENT DOCUMENTS

CN    103251406    8/2013
EP      3492000    6/2019
(Continued)

OTHER PUBLICATIONS

Extended European Search Report dated Nov. 24, 2020 issued in European Patent Application No. 20190126.1.
(Continued)

*Primary Examiner* — Nelson M Rosario
(74) *Attorney, Agent, or Firm* — H.C. Park & Associates, PLC

(57) ABSTRACT

A sensor unit including a plurality of driving electrodes, and a plurality of sensing electrodes, in which a first unit sensor is defined by R driving electrodes among the plurality of driving electrodes and S sensing electrodes among the plurality of sensing electrodes in a first driving mode, a second unit sensor is defined by P driving electrodes among the plurality of driving electrodes and Q sensing electrodes among the plurality of sensing electrodes in a second driving mode, P, Q, R and S are integers equal to or greater than 1, and R is smaller than P, and S is smaller than Q.

20 Claims, 23 Drawing Sheets

(51) Int. Cl.
　　　*A61B 5/00*　　　(2006.01)
　　　*G06F 3/041*　　　(2006.01)
　　　*H04M 1/02*　　　(2006.01)

(52) U.S. Cl.
　　　CPC ........ *G06F 3/0445* (2019.05); *H04M 1/0266* (2013.01); *H04M 2250/12* (2013.01); *H04M 2250/22* (2013.01)

(58) Field of Classification Search
　　　CPC .. G06F 3/0412; G06F 3/04166; G06F 3/0443; G06F 3/0445; G06F 3/0446; G06F 2203/04112; H01L 27/323; H04M 1/0266; H04M 2250/12; H04M 2250/22
　　　See application file for complete search history.

(56) References Cited

U.S. PATENT DOCUMENTS

| | | |
|---|---|---|
| 2018/0011598 A1 | 1/2018 | Ku et al. |
| 2018/0129341 A1 | 5/2018 | Bae et al. |
| 2018/0150176 A1 | 5/2018 | Kim et al. |
| 2019/0056823 A1 | 2/2019 | Stevenson et al. |
| 2019/0159717 A1 | 5/2019 | Park et al. |
| 2020/0209179 A1* | 7/2020 | Bohm .................. G01N 27/221 |

FOREIGN PATENT DOCUMENTS

| | | |
|---|---|---|
| KR | 10-0634544 | 10/2006 |
| KR | 10-0938403 | 1/2010 |
| KR | 2013-0134007 | 12/2013 |
| KR | 10-1462283 | 11/2014 |
| KR | 2016-0046965 | 5/2016 |
| KR | 10-2016-0112559 | 9/2016 |
| KR | 10-1856929 | 5/2018 |

OTHER PUBLICATIONS

Huang, Ting-Hsiang & Chou, Jung-Chuan & Sun, Tai-Ping & Hsiung, Shen-Kan. (2008). A device for skin moisture and environment humidity detection. Sensors and Actuators B: Chemical. 134. 206-212. 10.1016/j.snb.2008.04.030.

N. Sekiguchi, T. Komeda, H. Funakubo, R. Chabicovsky, J. Nicolics, G. Stangl, Microsensor for the measurement of water content in the human skin, Sensors and Actuators B: Chemical, vol. 78, Issues 1-3, 2001, pp. 326-330, ISSN 0925-4005,https://doi.org/10.1016/S0925-4005(01)00834-6.

Non-Final Office Action dated Apr. 1, 2021, issued to U.S. Appl. No. 16/913,666.

Notice of Allowance dated Jul. 12, 2021, issued to U.S. Appl. No. 16/913,666.

Extended European Search Report dated Feb. 3, 2023, issued in European Patent Application No. 20190126.1 (with English Translation).

* cited by examiner

SENSOR UNIT, DISPLAY DEVICE INCLUDING THE SAME, AND METHOD FOR MEASURING MOISTURE USING THE SAME

CROSS-REFERENCE TO RELATED APPLICATIONS

This application is a Continuation of U.S. patent application Ser. No. 16/913,666, filed on Jun. 26, 2020, which claims priority from and the benefit of Korean Patent Application No. 10-2019-0097397, filed on Aug. 9, 2019, each of which is hereby incorporated by reference for all purposes as if fully set forth herein.

BACKGROUND

Field

Exemplary embodiments of the invention relate generally to a sensor unit, a display device including the same, and a method for measuring moisture using the same.

Discussion of the Background

As the information-oriented society evolves, various demands for display devices are increasing. For example, display devices are being employed in a variety of electronic devices, such as smart phones, digital cameras, laptop computers, navigation devices, and smart televisions.

As display devices are employed in various electronic devices, display devices may be equipped with a variety of features. For example, many skin moisture meters capable of measuring a person's skin moisture have recently been used. However, since the skin moisture meters include an exposed electrode in contact with a user's skin, it has been difficult to directly apply the skin moisture meters to a display device.

The above information disclosed in this Background section is only for understanding of the background of the inventive concepts, and, therefore, it may contain information that does not constitute prior art.

SUMMARY

Display devices constructed according to exemplary embodiments of the invention include a sensor unit capable of measuring a person's skin moisture.

Exemplary embodiments also provide a display device including a sensor unit capable of measuring skin moisture, and a method of measuring moisture by the same.

Additional features of the inventive concepts will be set forth in the description which follows, and in part will be apparent from the description, or may be learned by practice of the inventive concepts.

A sensor unit according to an exemplary embodiment includes driving electrodes and sensing electrodes, driving lines connected to the driving electrodes, sensing lines connected to the sensing electrodes, a driving signal output unit configured to sequentially apply driving signals to every P driving lines in a first driving mode, in which P is a positive integer, and a detector configured to receive detection signals from every Q sensing lines in the first driving mode, in which Q is a positive integer and the first driving mode is for calculating a skin moisture content.

P may be greater than Q.

P may be equal to Q.

In the first driving mode, the driving signal output unit may be configured to apply the driving signals simultaneously to each of the P driving lines.

In the first driving mode, the driving signal output unit may be configured to apply the driving signals sequentially to every P driving lines for 1 to 1.5 seconds repeatedly.

In the first driving mode, the detector may be configured to convert the detection signals into digital detection data, and output the digital detection data.

In the first driving mode, a frequency of the driving signal may be in a range of about 50 kHz to about 500 kHz.

The driving signal output unit may be configured to apply the driving signals sequentially to every R driving lines in a second driving mode, in which R is a positive integer less than P, and the detector may be configured to receive the detection signals from S sensing lines in the second driving mode, in which S is a positive integer less than Q and the second driving mode is for detecting a touch.

R may be less than P, and S may be less than Q.

A time period during which the driving signals are sequentially applied to every P driving lines in the first driving mode may be longer than a time period during which the driving signals are sequentially applied to every R driving lines in the second driving mode.

A frequency of the driving signal in the first driving mode may be different from a frequency of the driving signal in the second driving mode.

A frequency of the driving signal in the first driving mode may be equal to a frequency of the driving signal in the second driving mode, the first driving mode may be a moisture measuring mode, and the second driving mode may be a touch sensing mode.

A display device according to another exemplary embodiment includes a display panel including a display unit configured to display images, and a sensor unit configured to measure a skin moisture content, the sensor unit including sensor electrodes including driving electrodes and sensing electrodes, driving lines connected to the driving electrodes, sensing lines connected to the sensing electrodes, a driving signal output unit configured to sequentially apply driving signals to every P driving lines in a first driving mode, wherein P is a positive integer, and a detector configured to receive detection signals from every Q sensing lines in the first driving mode, in which Q is a positive integer and the first driving mode is for calculating a skin moisture content.

The display device may further include a main processor, in which the detector may be configured to convert the detection signals into digital detection data and output the digital detection data in the first driving mode, and the main processor may be configured to calculate a skin moisture content based on the digital detection data.

The main processor may be configured to output skin moisture data including skin moisture content information according to the digital detection data.

The main processor may be configured to correct the digital detection data before calculating the skin moisture content according to the digital detection data.

The main processor may be configured to correct the digital detection data when at least one of a temperature is not in a predetermined temperature range and a humidity is not in a predetermined humidity range.

The corrected digital detection data may have a greater value than the digital detection data when the temperature is lower than a lower limit of the predetermined temperature range, and the corrected digital detection data may have a lower value than the digital detection data when the temperature is higher than an upper limit of the predetermined temperature range.

The main processor may be configured to increase the digital detection data when a protective film is disposed on the display panel.

The main processor may be configured to increase the digital detection data when the display panel is determined as being stationary.

A method of measuring moisture by a sensor unit according to another exemplary embodiment includes the steps of sequentially applying driving signals to every P driving lines, and receiving detection signals from every Q sensing lines, in which P and Q are positive integers, converting the detection signals into digital detection data, and calculating a skin moisture content based on the digital detection data, in which the skin moisture content increases as the digital detection data decreases.

The steps may further include correcting the digital detection data when at least one of a temperature is not in a predetermined temperature range and a humidity does is not in a predetermined humidity range.

The digital detection data may be corrected to have a greater value when the temperature is lower than a lower limit of the predetermined temperature range, and the digital detection data may be corrected to have a lower value when the temperature is higher than an upper limit of the predetermined temperature range.

The steps may further include increasing the digital detection data when a protective film is disposed on a display panel.

The steps may further include increasing the digital detection data if it is determined that a display panel is supported by a ground mass, such as a ground and an object.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
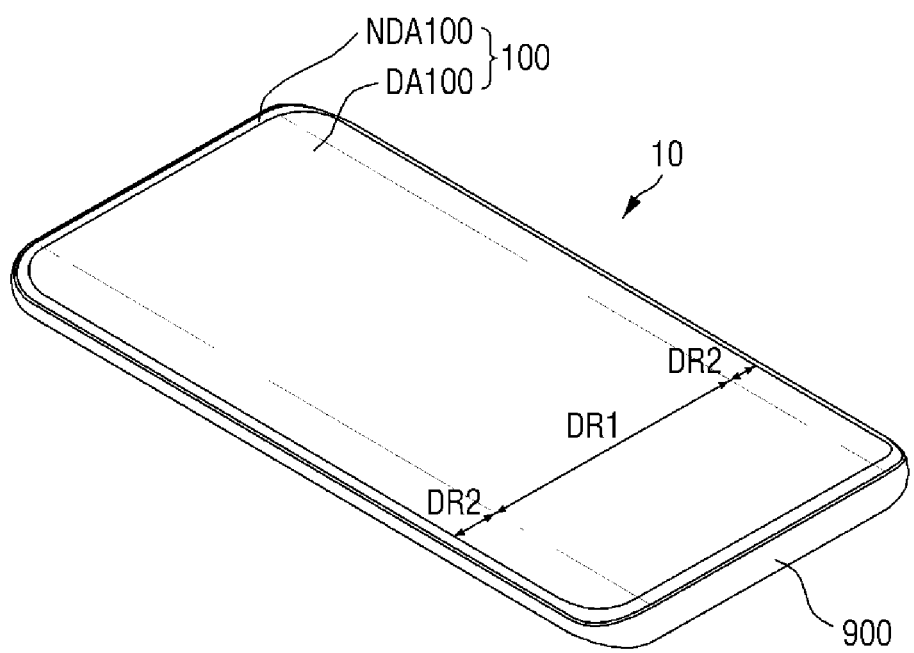
FIG. 1 is a perspective view of a display device according to an exemplary embodiment.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Figure 2:
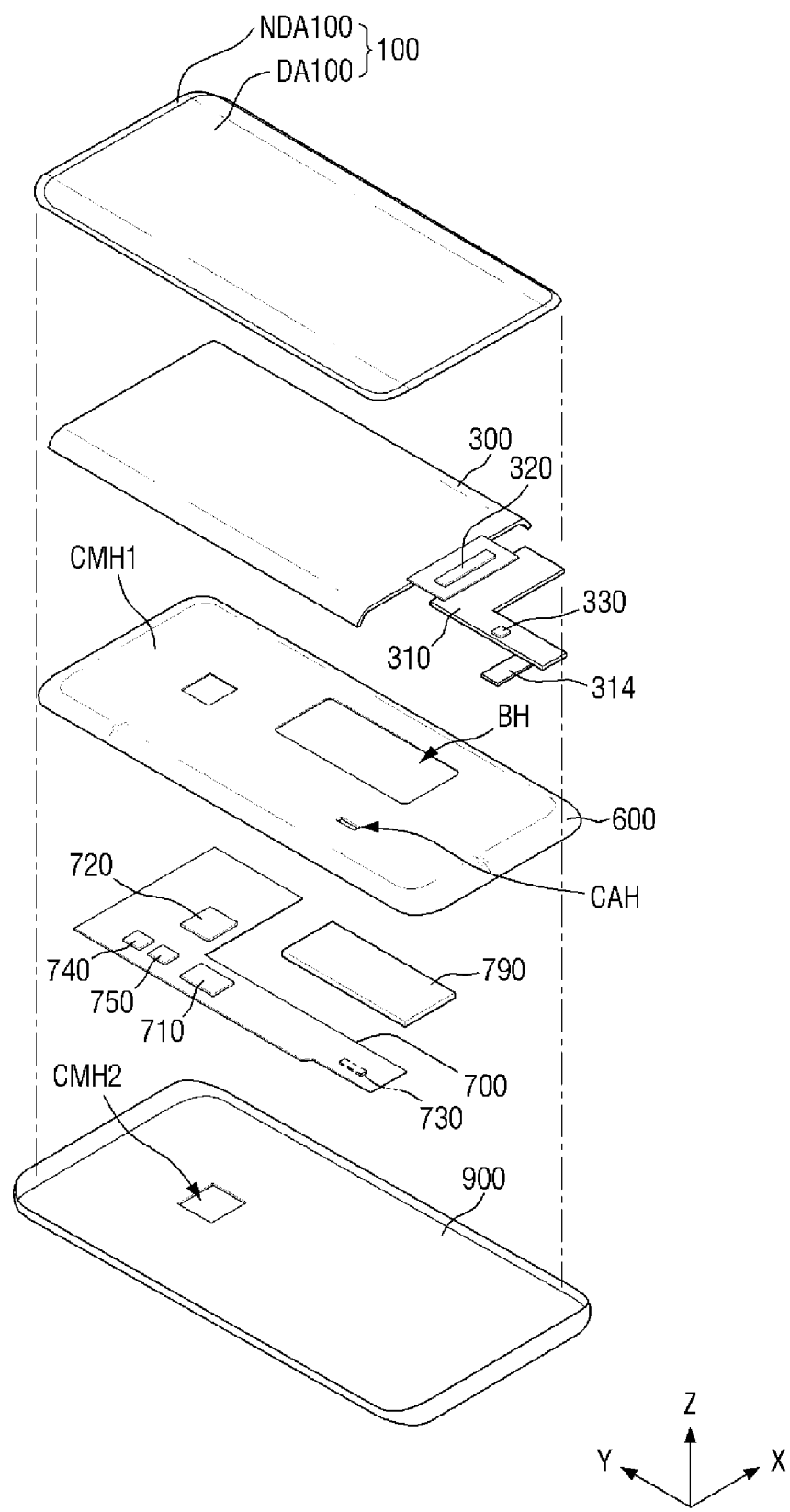
FIG. 2 is an exploded, perspective view of a display device according to an exemplary embodiment.

FIG. 1 is a perspective view of a display device according to an exemplary embodiment. FIG. 2 is an exploded, perspective view of a display device according to an exemplary embodiment.

Referring to FIGS. 1 to 2, a display device 10 according to an exemplary embodiment may display moving images or still images. The display device 1 may be used as a display screen of portable electronic devices, such as a mobile phone, a smart phone, a tablet PC, a smart watch, a watch phone, a mobile communications terminal, an electronic notebook, an electronic book, a portable multimedia player (PMP), a navigation device and a ultra mobile PC (UMPC), as well as a display screen of various products, such as a television, a notebook, a monitor, a billboard, and the Internet of Things.

The display device 10 according to an exemplary embodiment includes a cover window 100, a display panel 300, a display circuit board 310, a display driving circuit 320, a sensor driver 330, a bracket 600, a main circuit board 700, a battery 790, and a bottom cover 900.

As used herein, the term "upper side" refers to the side of the display panel 300 in the z-axis direction where the cover window 100 is disposed, whereas the term "lower side" refers to the opposite side of the display panel 300 in the z-axis direction where the bracket 600 is disposed. As used herein, the terms "left," "right," "upper" and "lower" sides indicate relative positions when the display panel 300 is viewed from the top. For example, the "left side" refers to the opposite direction indicated by the arrow of the x-axis, the "right side" refers to the direction indicated by the arrow of the x-axis, the "upper side" refers to the direction indicated by the arrow of the z-axis, and the "lower side" refers to the opposite direction indicated by the arrow of the z-axis.

The display device 10 may have substantially a rectangular shape when viewed from the top. For example, the display device 10 may have substantially a rectangular shape having shorter sides in a first direction (e.g., x-axis direction) and longer sides in a second direction (e.g., y-axis direction) when viewed from the top, as shown in FIGS. 1 and 2. Each of the corners where the short side in the first direction (e.g., x-axis direction) meets the longer side in the second direction (e.g., y-axis direction) may be rounded with a predetermined curvature or may be a right angle. However, the inventive concepts are not limited to a particular shape of the display device 10 when viewed from the top, and in some exemplary embodiments, the display device may have another polygonal shape, circular shape, or elliptical shape.

The display device 10 may include a first area DR1 which is formed flat, and a second area DR2 extended from the right and left sides of the first area DR1. The second area DR2 may be formed flat or may be curved. When the second area DR2 is formed flat, the angle formed by the first area DR1 and the second area DR2 may be an obtuse angle. When the second area DR2 is formed as a curved surface, the surface may have a constant curvature or a varying curvature.

Although the second areas DR2 are described as being extended from the left and right sides of the first area DR1 in FIG. 1, however, the inventive concepts are not limited thereto. In particular, the second area DR2 may be extended from only one of the right and left sides of the first area DR1. Alternatively, the second area DR2 may be extended from at least one of upper and lower sides of the first area DR1, as well as the left and right sides. Hereinafter, the second areas DR2 will be described as being disposed at the left and right edges of the display device 10, respectively, according to an exemplary embodiment.

The cover window 100 may be disposed on the display panel 300 to cover the upper surface of the display panel 300. Thus, the cover window 100 can protect the upper surface of the display panel 300.

The cover window 100 may include a transmissive portion DA100 corresponding to the display panel 300, and a non-transmissive portion NDA100 corresponding to the areas other than the display panel 300. The cover window 100 may be disposed in the first region DR1 and the second regions DR2. The transmissive portion DA100 may be disposed in a part of the first region DR1 and a part of each of the second regions DR2. The non-transmissive portion NDA100 may be opaque. Alternatively, the non-transmissive portion NDA100 may be formed as a decoration layer having a pattern that can be displayed to the user when no image is displayed.

The display panel 300 may be disposed under the cover window 100. The display panel 300 may be disposed to overlap the transmissive portion DA100 of the cover window 100. The display panel 300 may be disposed in the first area DR1 and the second areas DR2. Therefore, the image on the display panel 300 can be seen not only in the first area DR1 but also in the second areas DR2.

The display panel 300 may be a light-emitting display panel including light-emitting elements. For example, the display panel 300 may be an organic light-emitting display panel using organic light-emitting diodes including organic emissive layer, a micro light-emitting diode display panel using micro LEDs, a quantum-dot light-emitting display panel including quantum-dot light-emitting diodes including an quantum-dot emissive layer, or an inorganic light-emitting display panel using inorganic light-emitting elements including an inorganic semiconductor. Hereinafter, the display panel 300 will be described with reference to an organic light-emitting display panel according to an exemplary embodiment.

The display circuit board 310 and the display driving circuit 320 may be attached to one side of the display panel 300. One side of the display circuit board 310 may be attached to pads disposed on one side of the display panel 300 using an anisotropic conductive film or the like. The display circuit board 310 may be a flexible printed circuit board (FPCB) that can be bent, a rigid printed circuit board (PCB) that is rigid and not bendable, or a hybrid printed circuit board including a rigid printed circuit board and a flexible printed circuit board.

The display driving circuit 320 receives control signals and supply voltages through the display circuit board 310, and outputs signals and voltages for driving the display panel 300. The display driving circuit 320 may be implemented as an integrated circuit (IC). The display driving circuit 320 may be disposed on the display panel 300. For example, the display driving circuit 320 may be attached to the display panel 300 by a chip on glass (COG) technique, a chip on plastic (COP) technique, or an ultrasonic bonding. Alternatively, the display driving circuit 320 may be disposed on the display circuit board 310.

The sensor driver 330 may be disposed on the display circuit board 310. The sensor driver 330 may be implemented as an integrated circuit. The sensor driver 330 may be attached on the display circuit board 310. The sensor driver 330 may be electrically connected to sensor electrodes of a sensor electrode layer of the display panel 300 through the display circuit board 310. The sensor driver 330 may apply driving signals to driving electrodes among the sensor electrodes, and sense amounts of change in mutual capacitance between the driving electrodes and the sensing electrodes (hereinafter, referred to as "mutual capacitance") through sensing electrodes among the sensor electrodes. In this manner, it is possible to determine whether a user touches the display panel, as well as measuring the user's skin moisture. The user's touch may include a physical contact and a near proximity. A user's physical contact refers to when an object, such as the user's finger or a pen, is brought into contact with the cover window 100 of the display device 10 disposed on the sensor electrode layer. The near proximity refers to when an object, such as the user's finger or a pen, is close to but is spaced apart from a surface of the display device 10, such as hovering over the display device 10.

On the display circuit board 310, a power supply for supplying driving voltages for driving the pixels P, the scan driver 340, and the display driving circuit 320 of the display panel 300 may be further disposed. Alternatively, the power supply may be integrated with the display driving circuit 320, in which case, the display driving circuit 320 and the power supply may be implemented as a single integrated circuit.

The bracket 600 may be disposed under the display panel 300. The bracket 600 may include plastic, metal, or both of plastic and metal. In the bracket 600, a first camera hole CMH1, in which a camera device 720 is inserted, a battery hole BH, in which a battery is disposed, and a cable hole CAH, through which a cable 314 connected to the display circuit board 310, passes may be formed.

The main circuit board 700 and the battery 790 may be disposed under the bracket 600. The main circuit board 700 may be either a printed circuit board or a flexible printed circuit board.

The main circuit board 700 may include a main processor 710, a camera device 720, a main connector 730, an acceleration sensor 740, a gyro sensor 750, etc. The main processor 710, the acceleration sensor 740, and the gyro sensor 750 may be implemented as integrated circuits. In some exemplary embodiments, the acceleration sensor 740 and the gyro sensor 750 may be implemented as a single integrated circuit.

The camera device 720 may be disposed on both the upper and lower surfaces of the main circuit board 700. The main processor 710, the acceleration sensor 740, and the gyro sensor 750 may be disposed on the upper surface of the main circuit board 700, and the main connector 730 may be disposed on the lower surface of the main circuit board 700.

The main processor 710 may control the functions of the display device 10. For example, the main processor 710 may output digital video data to the display driving circuit 320 through the display circuit board 310, so that the display panel 300 displays images. In addition, the main processor 710 receives detection data from the sensor driver 330. The main processor 710 may determine whether there is a user's touch based on the detection data in a touch sensing mode, and may execute an operation associated with the user's physical contact or near proximity. For example, the main processor 710 may calculate the user's touch coordinates by analyzing the detection data in the touch sensing mode, and then may run an application indicated by an icon touched by the user or perform the operation. The main processor 710 may calculate the user's skin moisture by analyzing the detection data in a moisture measuring mode.

Hereinafter, the moisture measuring mode may also be referred to as a first driving mode, and the touch sensing mode may also be referred to as a second driving mode.

The main processor 710 may be an application processor, a central processing unit, or a system chip implemented as an integrated circuit.

The camera device 720 processes image frames, such as still image and video obtained by the image sensor in the camera mode, and outputs them to the main processor 710.

The cable 314 having passed through the cable hole CAH of the bracket 60 may be connected to main connector 730. Therefore, the main circuit board 700 may be electrically connected to the display circuit board 310.

The acceleration sensor 740 may detect acceleration in the first direction (e.g., x-axis direction), the second direction (e.g., y-axis direction), and the third direction (e.g., z-axis direction). The acceleration sensor 740 may output acceleration data including acceleration information in the first direction (e.g., x-axis direction), the second direction (e.g., y-axis direction), and the third direction (e.g., z-axis direction) to the main processor 710.

The gyro sensor 750 may detect angular velocity in the first direction (e.g., x-axis direction), the second direction (e.g., y-axis direction), and the third direction (e.g., z-axis direction). The gyro sensor 750 may output angular velocity data including angular velocity information in the first direction (e.g., x-axis direction), the second direction (e.g., y-axis direction), and the third direction (e.g., z-axis direction) to the main processor 710.

The main processor 710 may determine the inclination of the display device 10 and the rotation direction of the display device 10 based on the acceleration data from the acceleration sensor 740 and the angular velocity data from the gyro sensor 750. As such, the main processor 710 can determine whether the display device 10 is stationary based on the acceleration data and the angular velocity data.

The battery 790 may be disposed so as not to overlap the main circuit board 700 in the third direction (e.g., z-axis direction). The battery 790 may overlap with the battery hole BH of the bracket 600.

In some exemplary embodiments, a mobile communications module capable of transmitting/receiving a radio signal to/from at least one of a base station, an external terminal, and a server over a mobile communications network may be further mounted on the main circuit is board 700. The wireless signal may include various types of data depending on a voice signal, a video call signal, or a text/multimedia message transmission/reception.

The bottom cover 900 may be disposed under the main circuit board 700 and the battery 790. The bottom cover 900 may be fastened and fixed to the bracket 600. The bottom cover 900 may form the exterior of the lower surface of the display device 10. The bottom cover 900 may include plastic, metal, or plastic and metal.

A second camera hole CMH2 may be formed in the bottom cover 900, through which the lower surface of the camera device 720 is exposed. The positions of the camera device 720 and the first and second camera holes CMH1 and CMH2 in line with the camera device 720 are not limited to those shown in FIG. 2.

Figure 3:
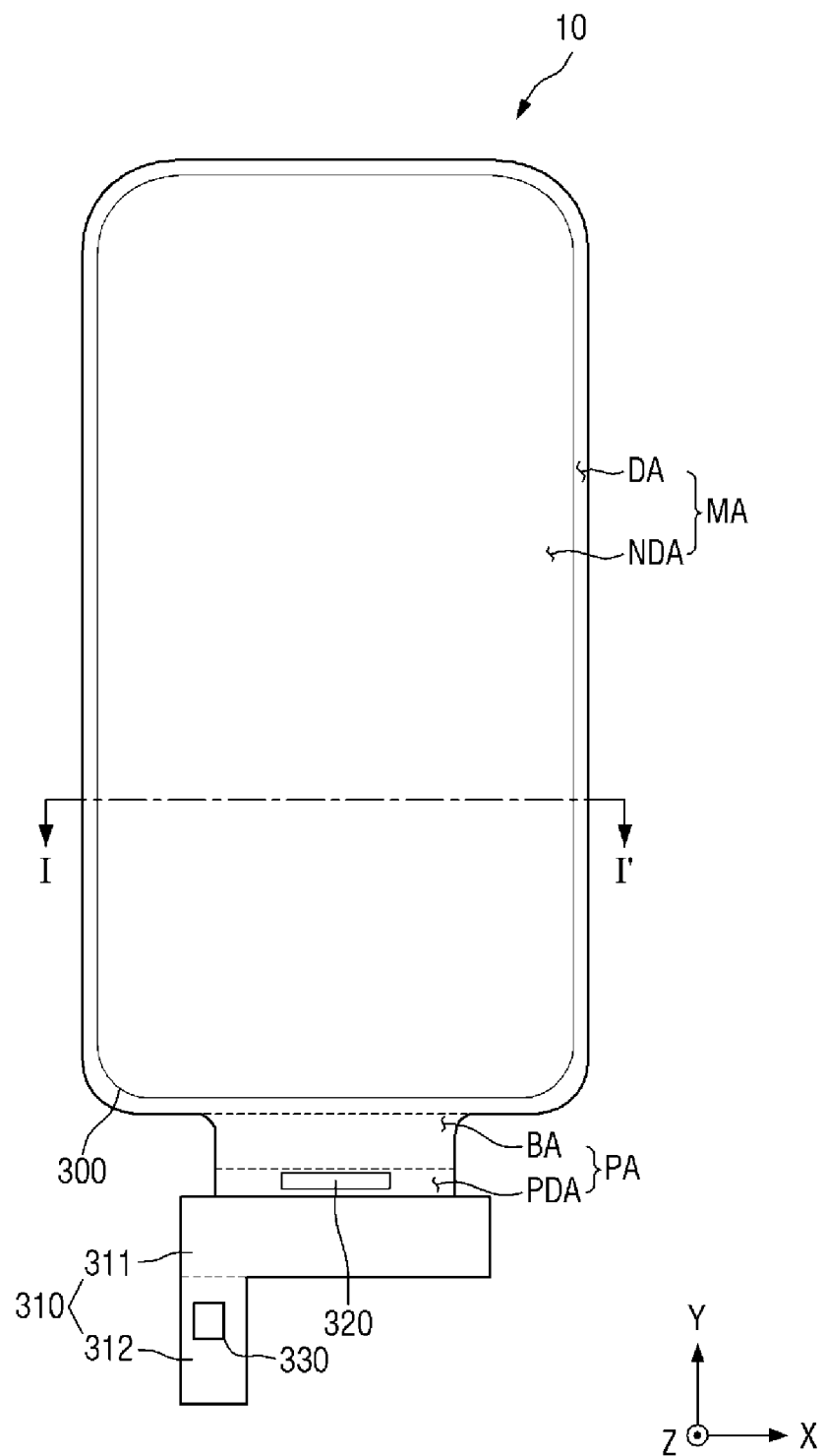
FIG. 3 is a plan view showing a display panel according to an exemplary embodiment.
Figure 4:
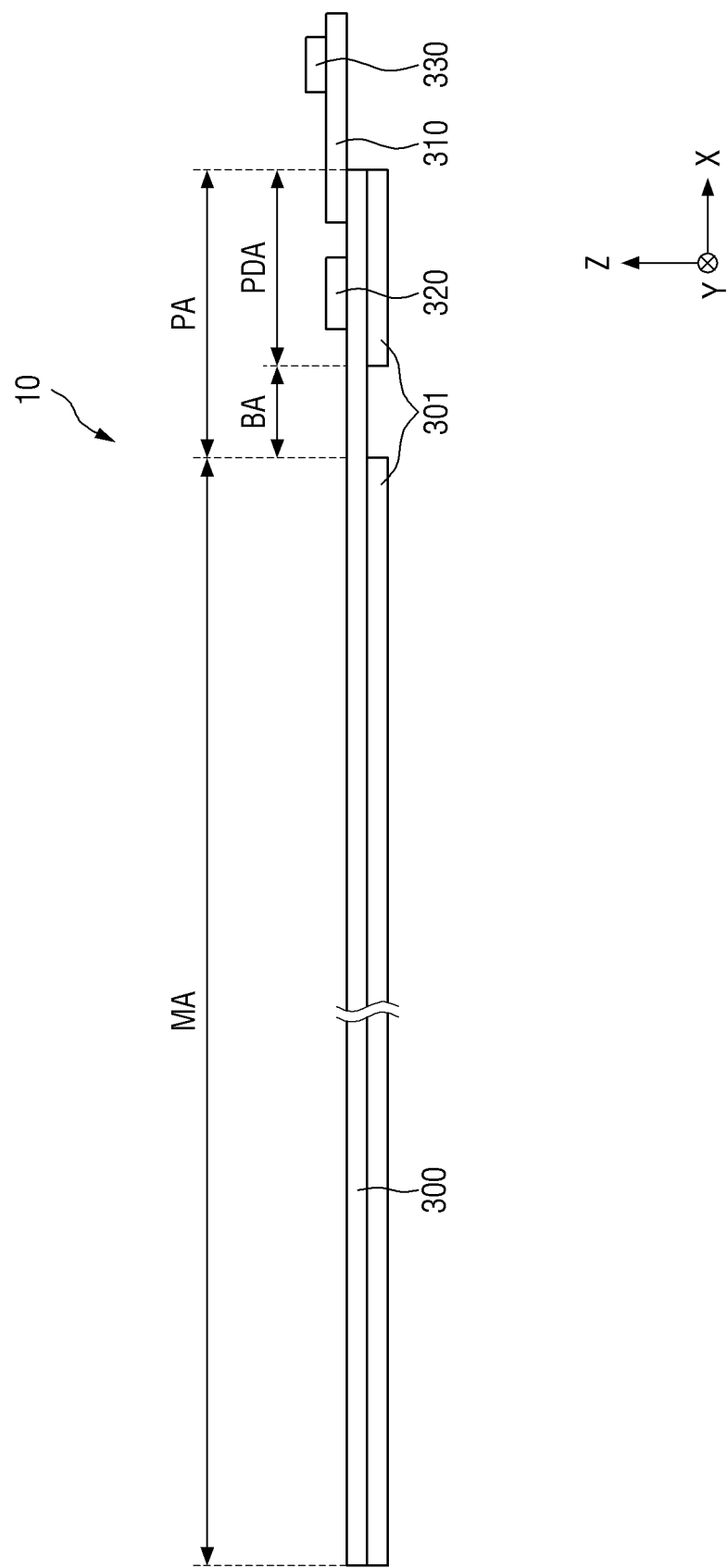
FIGS. 4 and 5 are cross-sectional views showing a display device according to an exemplary embodiment.
Figure 5:
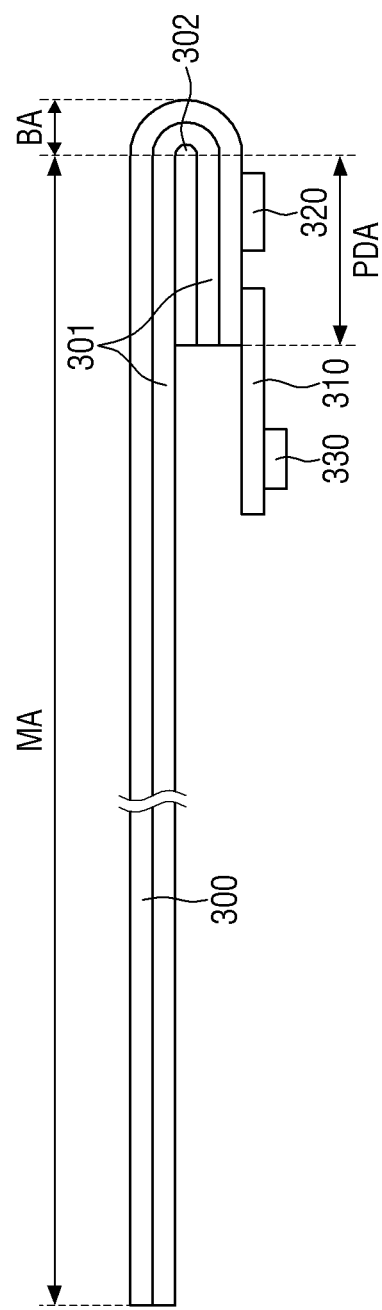

FIG. 3 is a plan view of a display panel according to an exemplary embodiment. FIGS. 4 and 5 are cross-sectional views of a display device according to an exemplary embodiment.

Referring to FIGS. 3 to 5, the display panel 300 according to an exemplary embodiment may be one of an organic light-emitting display panel, a liquid-crystal display panel, a plasma display panel, a field emission display panel, an electrophoretic display panel, an electrowetting display panel, and a quantum-dot light-emitting display panel, an inorganic light-emitting display panel, and a micro LED display device. Hereinafter, the display panel 300 will be described with reference to an organic light-emitting display device. However, the inventive concepts are not limited thereto.

The display panel 300 may include a main area MA and a protruding area PA protruding from one side of the main area MA.

The main area MA may be formed in a rectangular plane having shorter sides in a first direction (e.g., x-axis direction) and longer sides in a second direction (e.g., y-axis direction) intersecting the first direction (e.g., x-axis direction). Each of the corners where the short side in the first direction (e.g., x-axis direction) meets the longer side in the second direction (e.g., y-axis direction) may be rounded with a predetermined curvature or may be a right angle. The shape of the display device 10 when viewed from the top is not limited to a quadrangular shape, but may be formed in another polygonal shape, circular shape, or elliptical shape in some exemplary embodiments. The main area MA may be, but is not limited to, formed to be flat. The main area MA may include curved portions formed at left and right ends thereof. The curved portions may have a constant curvature or varying curvatures.

The main area MA may include a display area DA where pixels are formed to display images, and a non-display area NDA around the display area DA.

In addition to the pixels, scan lines, data lines, and power lines connected to the pixels may be disposed in the display area DA. When the main area MA includes a curved portion, the display area DA may be disposed on the curved portion. In this case, images of the display panel 300 can also be seen on the curved portion.

The non-display area NDA may be defined as the area from the outer side of the display area DA to the edge of the display panel 300. In the non-display area NDA, a scan driver for applying scan signals to scan lines, and link lines connecting the data lines with the display driving circuit 320 may be disposed.

The protruding area PA may protrude from one side of the main area MA. For example, the protruding area PA may protrude from the lower side of the main area MA as shown in FIG. 3. The length of the protruding area PA in the first direction (e.g., x-axis direction) may be less than the length of the main area MA in the first direction (e.g., x-axis direction).

The protruding area PA may include a bending area BA and a pad area PDA. In this case, the pad area PDA may be disposed on one side of the bending area BA, and the main area MA may be disposed on the opposite side of the bending area BA. For example, the pad area PDA may be disposed on the lower side of the bending area BA, and the main area MA may be disposed on the upper side of the bending area BA.

The display panel 300 may be formed to be flexible so as to be curved, bent, folded or rolled. As such, the display panel 300 may be bent at the bending area BA in the thickness direction. As shown in FIG. 4, one surface of the pad area PDA of the display panel 300 may face upward before the display panel 300 is bent. As shown in FIG. 5, the surface of the pad area PDA of the display panel 300 may face downward after the display panel 300 is bent. In this case, since the pad area PDA is disposed under the main area MA, the pad area PDA may overlap the main area MA.

Pads electrically connected to the display driving circuit 320 and the display circuit board 310 may be disposed in the pad area PDA of the display panel 300.

A cover panel sheet 301 may be disposed under the display panel 300. The cover panel sheet 301 may be attached to the lower surface of the display panel 300 by an adhesive member, or the like. The adhesive member may be a pressure-sensitive adhesive (PSA).

The cover panel sheet 301 may include a light-absorbing member for absorbing light incident from outside, a buffer member for absorbing external impact, and a heat dissipating member for efficiently discharging heat from the display panel 300.

The light-absorbing member may be disposed under the display panel 300. The light-absorbing member blocks the transmission of light to prevent the elements disposed thereunder from being seen from above the display panel 300, such as the display circuit board 310. The light-absorbing member may include a light-absorbing material, such as a black pigment and a black dye.

The buffer member may be disposed under the light-absorbing member. The buffer member absorbs an external impact to prevent the display panel 300 from being damaged. The buffer member may have a single layer or multiple layers structure. For example, the buffer member may be formed of a polymer resin, such as polyurethane, polycarbonate, polypropylene and polyethylene, or may be formed of a material having elasticity, such as a rubber and a sponge obtained by foaming a urethane-based material or an acrylic-based material. The buffer member may be a cushion layer.

The heat dissipating member may be disposed under the buffer member. The heat-dissipating member may include a first heat dissipation layer including graphite or carbon nanotubes, and a second heat dissipation layer formed of a thin metal film, such as copper, nickel, ferrite, and silver, which can block electromagnetic waves and have high thermal conductivity.

In order to easily bend the display panel 300, the cover panel sheet 301 may not be disposed in the bending area BA of the display panel 300 as shown in FIG. 4. Since the display panel 300 is bent in the bending area BA such that the pad area PDA is disposed under the main area MA, the display panel 300 may overlap the main area MA. Accordingly, the cover panel sheet 301 disposed in the main area MA of the display panel 300 and the cover panel sheet 301 disposed in the pad area PDA of the display panel 300 may be attached together by an adhesive member 302. The adhesive member 302 may be a pressure-sensitive adhesive.

The display driving circuit 320 outputs signals and voltages for driving the display panel 300. For example, the display driving circuit 320 may apply data voltages to the data lines. In addition, the display driving circuit 320 may apply supply voltage to the power line, and may apply scan control signals to the scan driver. The display driving circuit 320 may be implemented as an integrated circuit (IC), and may be attached to the display panel 300 in a pad area PDA by a chip on glass (COG) technique, a chip on plastic (COP) technique, or an ultrasonic bonding. For example, the display driving circuit 320 may be mounted on the display circuit board 310.

Pads may include display pads electrically connected to the display driving circuit 320 and sensor pads electrically connected to sensor lines.

The display circuit board 310 may be attached on the pads using an anisotropic conductive film or the like. In this manner, the lead lines of the display circuit board 310 may be electrically connected to the pads. The display circuit board 310 may be a flexible printed circuit board, a printed circuit board, or a flexible film, such as a chip on film.

The sensor driver 330 may be connected to the sensor electrodes of the sensor electrode layer SEL of the display panel 300. The sensor driver 330 applies driving signals to the sensor electrodes of the sensor electrode layer SEL, and measures mutual capacitances of the sensor electrodes. The driving signals may have driving pulses. The sensor driver 330 can determine whether there is a user's touch or nearby proximity based on the mutual capacitances. As described above, a user's touch may refer to when an object, such as the user's finger or a pen, is brought into contact with a surface of the display device 10 disposed on the sensor electrode layer SEL, and the user's near proximity may refer to when an object, such as the user's finger and a pen, is hovering over a surface of the display device 10.

The sensor driver 330 may be disposed on the display circuit board 310. The sensor driver 330 may be implemented as an integrated circuit (IC) and may be mounted on the display circuit board 310.

Figure 6:
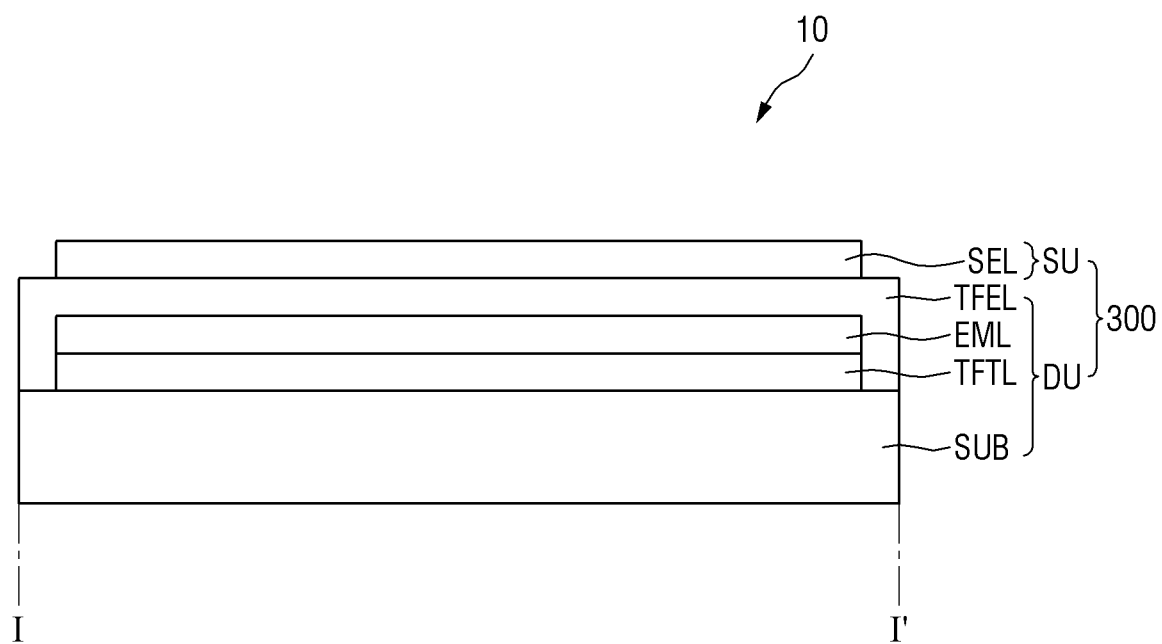
FIG. 6 is a cross-sectional view taken along line I-I' of FIG. 2.

FIG. 6 is a cross-sectional view taken along line I-I' of FIG. 2. Referring to FIG. 6, the display panel 300 may include a display unit DU and a second unit SU. The display unit DU may have a substrate SUB, a thin-film transistor layer TFTL disposed on the substrate SUB, an emission material layer EML, and a thin-film encapsulation layer TFEL. The sensor unit SU may have a sensor electrode layer SEL.

The substrate SUB may be made of an insulating material, such as glass, quartz, and a polymer resin. The polymer material may include polyethersulphone (PES), polyacrylate (PA), polyacrylate (PAR), polyetherimide (PEI), polyethylene naphthalate (PEN), polyethylene terephthalate (PET), polyphenylene sulfide (PPS), polyallylate, polyimide (PI), polycarbonate (PC), cellulose triacetate (CAT), cellulose acetate propionate (CAP), or a combination thereof. Alternatively, the substrate SUB may include a metallic material.

The substrate SUB may be a rigid substrate or a flexible substrate that can be bent, folded, rolled, and so on. When the substrate SUB is a flexible substrate, the substrate may include polyimide (PI), without being limited thereto.

Figure 7:
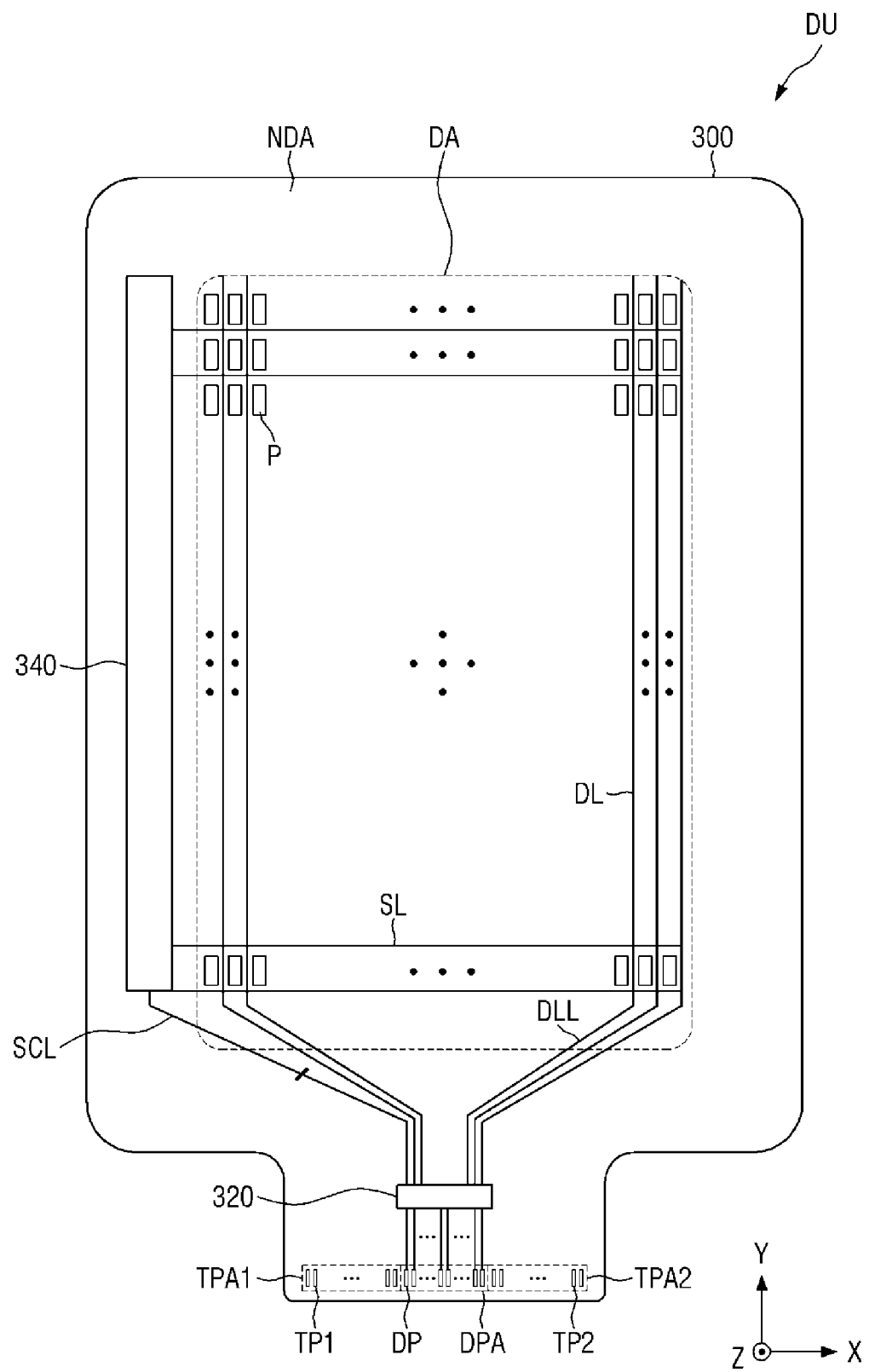
FIG. 7 is a plan view of the display unit of FIG. 5 according to an exemplary embodiment.

The thin-film transistor layer TFTL may be disposed on the substrate SUB. On the thin-film transistor layer TFTL, scan lines, data lines, power supply lines, scan control lines, routing lines connecting the pads with the data lines may be formed, as well as thin-film transistors in the pixels. Each of the thin-film transistors may include a gate electrode, a semiconductor layer, a source electrode, and a drain electrode. When the scan driver 340 is formed in the non-display area NDA of the display panel 300 as shown in FIG. 7, the scan driver 340 may include thin-film transistors.

The thin-film transistor layer TFTL may be disposed in the display area DA and the non-display area NDA. More particularly, the thin-film transistors in the pixels, the scan lines, the data lines, and the power supply lines on the thin-film film transistor layer TFTL may be disposed in the display area DA. The scan control lines and the link lines on the thin-film transistor layer TFTL may be disposed in the non-display area NDA.

The emission material layer EML may be disposed on the thin-film transistor layer TFTL. The light-emitting element layer EML may include pixels including a first electrode, an emissive layer, a second electrode, and a pixel-defining layer. The emissive layer may be an organic emissive layer including an organic material. The emissive layer may include a hole transporting layer, an organic light-emitting layer, and an electron transporting layer. When a voltage is applied to the first electrode, and a cathode voltage is applied to the second electrode through the thin-film transistor disposed on the thin-film transistor layer TFTL, the holes and electrons move to the organic light-emitting layer through the hole transporting layer and the electron transporting layer, respectively, and be combined in the organic light-emitting layer to emit light. The pixels on the light-emitting element layer EML may be disposed in the display area DA.

The thin-film encapsulation layer TFEL may be disposed on the light-emitting element layer EML. The thin-film encapsulation layer TFEL may prevent oxygen or moisture from permeating into the light-emitting element layer EML. As such, the thin-film encapsulation layer TFEL may include at least one inorganic layer. The inorganic layer may be, but not limited to, a silicon nitride layer, a silicon oxynitride layer, a silicon oxide layer, a titanium oxide layer, or an aluminum oxide layer. In addition, the thin-film encapsulation layer TFEL protects the light-emitting element layer EML from foreign substances, such as dust. To this end, the thin-film encapsulation layer TFEL may include at least one organic layer. The organic layer may be formed of, but is not limited to, an acryl resin, an epoxy resin, a phenolic resin, a polyamide resin, and a polyimide resin.

The thin-film encapsulation layer TFEL may be disposed in the display area DA as well as the non-display area NDA. More particularly, the thin-film encapsulation layer TFEL may cover the display area DA and the emission material layer EML, and may cover the thin-film transistor layer TFTL in the non-display area NDA.

The sensor electrode layer SEL may be disposed on the thin-film encapsulation layer TFEL. As the sensor electrode layer SEL is disposed directly on the thin-film encapsulation layer TFEL, the thickness of the display device 10 can be reduced, as compared with when the sensor electrode layer SEL is disposed on a separate touch panel to be attached on the thin-film encapsulation layer TFEL.

Figure 8:
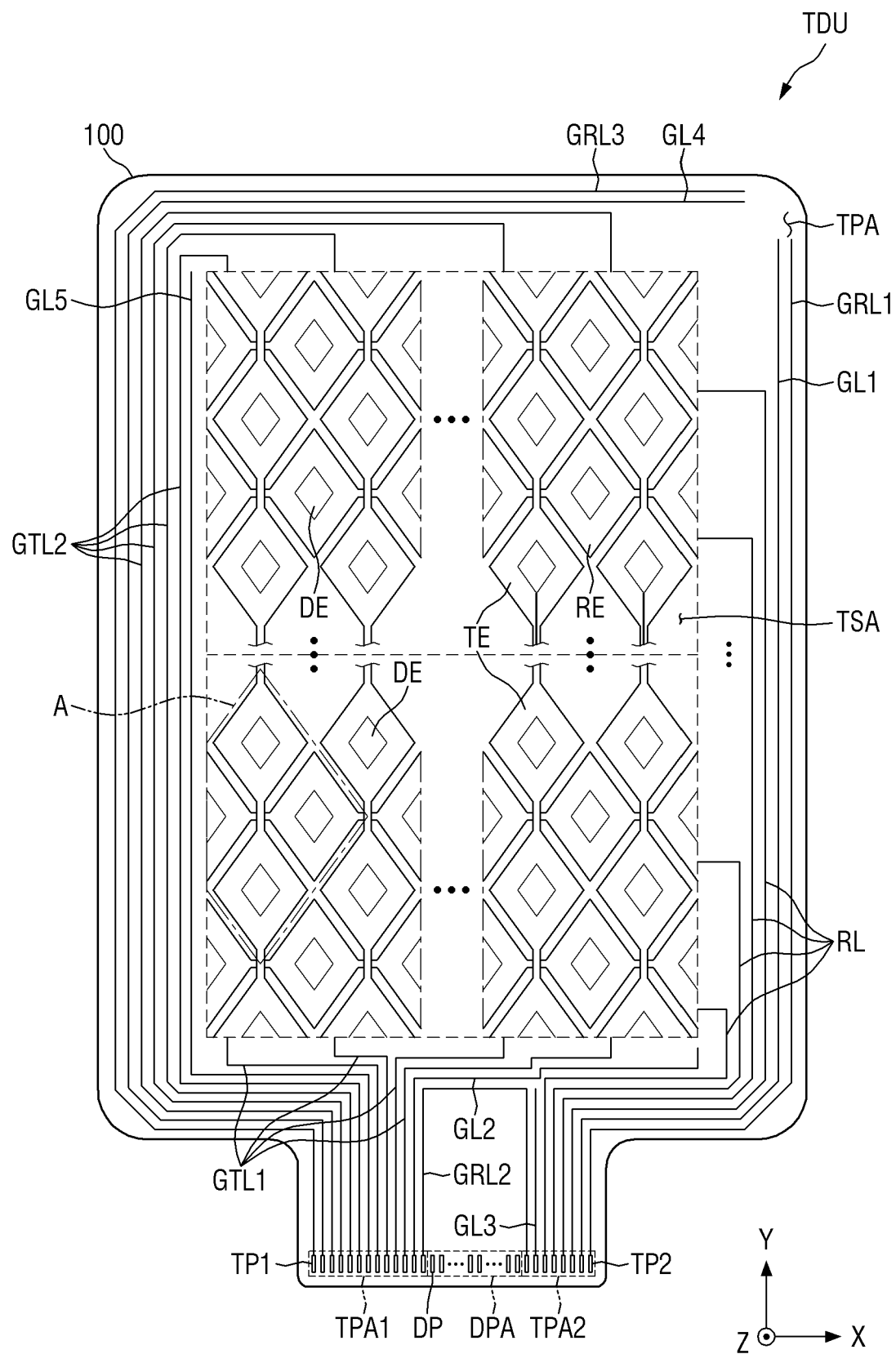
FIG. 8 is a plan view of the sensor unit of FIG. 5 according to an exemplary embodiment.

The sensor electrode layer SEL may include sensor electrodes for capacitive sensing, and sensor lines connecting the sensor pads with the sensor electrodes. The sensor electrodes of the sensor electrode layer SEL may be disposed in a sensor area TSA overlapping the display area DA, as shown in FIG. 8. The sensor electrodes of the sensor electrode layer SEL may be disposed in a sensor peripheral area TPA overlapping the non-display area NDA, as shown in FIG. 8.

A polarizing film may be disposed on the sensor electrode layer SEL. The polarizing film may include a linear polarizer and a phase retardation film, such as a $\lambda/4$ (quarter-wave) plate. In this case, the phase retardation film may be disposed on the sensor electrode layer SEL, and the linear polarizer may be disposed on the phase retardation film. In addition, a cover window may be disposed on the polarizing film. The cover window may be attached onto the polarizing film by a transparent adhesive member, such as an optically clear adhesive (OCA) film.

FIG. 7 is a plan view of the display unit of FIG. 6 according to an exemplary embodiment.

FIG. 7 exemplarily shows only pixels P, scan lines SL, data lines DL, scan control lines SCL, fan-out lines DLL, a scan driver 340, a display driving circuit 320, and display pads DP of the display unit DU.

Referring to FIG. 7, the scan lines SL, the data lines DL, and the pixels P are disposed in the display area DA. The scan lines SL may be arranged in the first direction (e.g., x-axis direction), while the data lines DL may be arranged in the second direction (e.g., y-axis direction) intersecting the first direction (e.g., x-axis direction).

Each of the pixels P may be connected to at least one of the scan lines SL and at least one of the data lines DL. Each of the pixels P may include thin-film transistors including a driving transistor and at least one switching transistor, a light-emitting element, and a capacitor. When a scan signal is applied from a scan line SL, each of the pixels P receives a data voltage of a data line DL, and supplies a driving current to the light-emitting element according to the data voltage applied to the gate electrode to cause emission of light. Although the light-emitting element is described with reference to an organic light-emitting element including a first electrode, an organic emitting layer, and a second electrode, however, the inventive concepts are not limited thereto. For example, in some exemplary embodiments, the light-emitting element may be implemented as a quantum-dot light-emitting element including a first electrode, a quantum-dot emitting layer, and a second electrode, as an inorganic light-emitting element including a first electrode, an inorganic emitting layer having an inorganic semiconductor, and a second electrode, or a micro light-emitting element including a micro light-emitting diode.

The scan driver 340 is connected to the display driving circuit 320 through a plurality of scan control lines SCL. Accordingly, the scan driver 340 may receive the scan control signal of the display driving circuit 320. The scan driver 340 generates scan signals according to a scan control signal, and supplies the scan signals to the scan lines SL.

Although the scan driver 340 is illustrated as being formed in the non-display area NDA on the left side of the display area DA as shown in FIG. 5, however, the inventive concepts are not limited thereto. For example, in some exemplary embodiments, the scan driver 340 may be formed in the non-display area NDA on the left side as well as in the non-display area NDA on the right side of the display area DA.

The display driving circuit 320 is connected to the display pads DP and receives digital video data and timing signals. The display driving circuit 320 converts the digital video data into analog positive/negative data voltages, and supplies the analog positive/negative data voltages to the data lines DL through the fan-out lines DLL. In addition, the display driving circuit 320 generates and supplies a scan control signal for controlling the scan driver 340 through the scan control lines SCL. The pixels P to which the data voltages are supplied are selected by the scan signals of the scan driver 340, and the data voltages are supplied to the selected pixels P. The display driving circuit 320 may be implemented as an integrated circuit (IC) and may be attached to the substrate SUB by a chip on glass (COG) technique, a chip on plastic (COP) technique, or an ultrasonic bonding. However, the inventive concepts are not limited thereto. For example, in some exemplary embodiments, the display driving circuit 320 may be mounted on the display circuit board 310.

As shown in FIG. 7, the display panel 300 may include display pads DP electrically connected to the display driving circuit 320, and sensor pads TP1 and TP2 electrically connected to the sensor lines. A display pad area DPA, in which the display pads DP are disposed, may be disposed between a first sensor pad area TPA1 in which the first sensor pads TP1 are disposed and a second sensor pad area TPA2 in which the second sensor pads TP2 are disposed. As shown in FIG. 7, the display pad area DPA may be disposed at the center of one end of the protruding area PA, the first sensor pad area TPA1 may be disposed at the left side of the end of the protruding area PA, and the second sensor pad area TPA2 may be disposed on the right side of the end of the protruding area PA.

The display circuit board 310 may be attached on the display pads DP and the sensor pads TP1 and TP2 using an anisotropic conductive film or the like. Accordingly, the lead lines of the display circuit board 310 may be electrically connected to the display pads DP and the sensor pads TP1 and TP2. The display circuit board 310 may be a flexible printed circuit board, a printed circuit board, or a flexible film, such as a chip on film.

The sensor driver 330 may be connected to the sensor electrodes of the sensor unit of the display panel 300. The sensor driver 330 applies driving signals to the sensor electrodes, and senses mutual capacitances of the sensor electrodes. The driving signals may have driving pulses. The sensor driver 330 may be disposed on the display circuit board 310. The sensor driver 330 may be implemented as an integrated circuit, and may be mounted on the display circuit board 310.

FIG. 8 is a plan view showing the sensor unit of FIG. 5 according to an exemplary embodiment.

Referring to FIG. 8, the sensor electrodes of the sensor unit SU according to an exemplary embodiment include the two kinds of electrodes, e.g., the driving electrodes TE and the sensing electrodes RE connected through the connection portions BE1. The sensor unit SU may be formed as two layers and perform capacitive sensing by applying the driving signals to the driving electrodes TE and then sensing the amounts of change in mutual capacitances through the sensing electrodes RE. However, the inventive concepts are not limited thereto. For example, in some exemplary embodiments, the sensor electrodes TE and RE of the sensor unit SU may include the driving electrodes TE and the sensing electrodes RE without the connection portions BE1, and may be formed as one layer for capacitive sensing. Alternatively, the sensor unit SU may be driven in one layer for self-capacitance sensing that senses amounts of change in self-capacitances using one kind of electrodes.

FIG. 8 exemplarily shows only sensor electrodes TE and RE, conductive patterns DE, sensor lines TL and RL, sensor pads TP1 and TP2, guard lines GL1 to GL5, and ground lines GRL1 to GRL3.

Referring to FIG. 8, the sensor unit SU includes a sensor area TSA for sensing a user's touch, and a sensor peripheral area TPA disposed around the sensor area TSA. The sensor area TSA may overlap the display area DA of the display panel 300, and the sensor peripheral area TPA may overlap the non-display area NDA of the display unit DU.

The sensor electrodes TE and RE may include first sensor electrodes TE and second sensor electrodes RE. In the illustrated exemplary embodiment shown in FIG. 8, the first sensor electrode is the driving electrode TE, and the second sensor electrode is the sensing electrode RE. In FIG. 8, the driving electrodes TE, the sensing electrodes RE, and the conductive patterns DE each have a diamond shape when viewed from the top, but the inventive concepts are not limited thereto.

The sensing electrodes RE may be arranged in the first direction (e.g., x-axis direction) and electrically connected to one another. The driving electrodes TE may be arranged in the second direction (e.g., y-axis direction) crossing the first direction (e.g., x-axis direction) and may be electrically connected to one another. The driving electrodes TE may be electrically separated from the sensing electrodes RE. The driving electrodes TE may be spaced apart from the sensing electrodes RE. The driving electrodes TE may be arranged in parallel in the second direction (e.g., y-axis direction). In order to electrically separate the sensing electrodes RE from the driving electrodes TE at their intersections, the driving electrodes TE adjacent to each other in the second direction (e.g., y-axis direction) may be connected through the first connection portion BE1, and the sensing electrodes RE adjacent to each other in the first direction (e.g., x-axis direction) may be connected through second connection portion BE2.

The conductive patterns DE may be electrically separated from the driving electrodes TE and the sensing electrodes RE. The driving electrodes TE, the sensing electrodes RE, and the conductive patterns DE may be disposed apart from each other. The conductive patterns DE may be surrounded by the driving electrodes TE and the sensing electrodes RE, respectively. The parasitic capacitance between the second electrode of the emission material layer EML and the driving electrode TE or the sensing electrode RE may be reduced due to the conductive patterns DE. When the parasitic capacitance is reduced, the mutual capacitance between the driving electrode TE and the sensing electrode RE can be charged more quickly. However, as the area of the driving electrode TE and the sensing electrode RE is reduced due to the conductive patterns DE, the mutual capacitance between the driving electrode TE and the sensing electrode RE may be reduced, and may become more affected by noise. As such, the area of the conductive patterns DE may be determined in consideration of the trade-off between the parasitic capacitance and the mutual capacitance.

The sensor lines TL, RL, and PL may be disposed in the sensor peripheral area TPA. The sensor lines TL and RL may include sensing lines RL connected to the sensing electrodes RE, and a first group of driving lines GTL1 and a second group of driving lines GTL2 connected to the driving electrodes TE.

The sensing electrodes RE disposed on one side of the sensor area TSA may be connected to the sensing lines RL. For example, some of the sensing electrodes RE electrically connected in the first direction (e.g., x-axis direction) that are disposed at the right end may be connected to the sensing lines RL, as shown in FIG. 8. The sensing lines RL may be connected to second sensor pads TP2. As such, the sensor driver 330 may be electrically connected to the sensing electrodes RE.

The driving electrodes TE disposed near one side of the sensor area TSA may be connected to the first group of driving lines GTL1, and the driving electrodes TE disposed near the other side of the sensor area TSA may be connected to the second group of driving lines GTL2. For example, as shown in FIG. 8, some of the driving electrodes TE electrically connected to one another in the second direction (e.g., y-axis direction) on the lowermost side may be connected to the first group of driving line GTL1, while some of the driving electrodes TE disposed on the uppermost side may be connected to the second group of driving line GTL2. The second group of driving lines GTL2 may be connected to the driving electrodes TE on the upper side of the sensor area TSA via the left outer side of the sensor area TSA. The first group of driving lines GTL1 and the second group of driving lines GTL2 may be connected to the first sensor pads TP1. As such, the sensor driver 330 may be electrically connected to the driving electrodes TE.

The first guard line GL1 may be disposed on the outer side of the outermost one of the sensing lines RL. In addition, the first ground line GRL1 may be disposed on the outer side of the first guard line GL1. As shown in FIG. 8, the first guard line GL1 may be disposed on the right side of the rightmost one of the sensing lines RL, and the first ground line GRL1 may be disposed on the right side of the first guard line GL1.

A second guard line GL2 may be disposed between the innermost one of the sensing lines RL and the rightmost one of the first group of driving lines GTL1. As shown in FIG. 8, the innermost one of the sensing lines RL may be the leftmost one of the sensing lines RL. In addition, the second guard line GL2 may be disposed between the rightmost one of the first group of driving lines GTL1 and the second ground line GRL2.

A third guard line GL3 may be disposed between the innermost one of the sensing lines RL and the second ground line GRL2. The second ground line GRL2 may be connected to the rightmost one of the first sensor pads TP1 and the leftmost one of the second sensor pads TP2.

A fourth guard line GL4 may be disposed on the outer side of the outermost one of the second group of driving lines GTL2. As shown in FIG. 8, the fourth guard line GL4 may be disposed on the left side of the leftmost one of the second group of driving lines GTL2.

In addition, the third ground line GRL3 may be disposed on the outer side of the fourth guard line GL4. As shown in FIG. 8, the fourth guard line GL4 may be disposed on the left side and upper side of the leftmost and uppermost one of the second group driving lines GTL2, and the third ground line GRL3 may be disposed on the left side and upper side of the fourth guard line GL4.

A fifth guard line GL5 may be disposed on the inner side of the innermost one of the second group of driving lines GTL2. As shown in FIG. 8, the fifth guard line GL5 may be disposed between the rightmost one of the second group of driving lines GTL2 and the sensing electrodes RE.

A ground voltage may be applied to the first ground line GRL1, the second ground line GRL2, and the third ground line GRL3. In addition, a ground voltage may be applied to the first guard line GL1, the second guard line GL2, the third guard line GL3, the fourth guard line GL4, and the fifth guard line GL5.

According to the illustrated exemplary embodiment shown in FIG. 8, the driving electrodes TE adjacent to each other in the second direction (e.g., y-axis direction) are electrically connected to each other, while the driving electrodes TE adjacent to each other the first direction (e.g., x-axis direction) are electrically insulated from each other. In addition, the sensing electrodes RE adjacent to each other in the first direction (e.g., x-axis direction) are electrically connected to each other, while the sensing electrodes RE adjacent to each other in the second direction (e.g., y-axis direction) are electrically insulated from each other. In this manner, mutual capacitances may be formed at intersections of the driving electrodes TE and the sensing electrodes RE.

In addition, according to the illustrated exemplary embodiment shown in FIG. 8, the first guard line GL1 is disposed between the outermost one of the sensing lines RL and the first ground line GRL1, so that the influence from a change in the voltage of the first ground line GRL1 to the outermost one of the sensing lines RL may be reduced. The second guard line GL2 is disposed between the innermost one of the sensing lines RL and the outermost one of the first group of driving lines GTL1. In this manner, the second guard line GL2 can reduce the influence from a change in the voltage to the innermost one of the sensing lines RL and to the outermost one of the first group of driving lines GTL1. The third guard line GL3 is disposed between the innermost one of the sensing lines RL and the second ground line GRL2, so that the influence from a change in the voltage of the second ground line GRL2 to the innermost one of the sensing lines RL may be reduced. The fourth guard line GL4 is disposed between the outermost one of the second group of driving lines GTL2 and the third ground line GRL3, so that the influence from a change in the voltage of the third ground line GRL3 to the second group of driving line GTL2 may be reduced. The fifth guard line GL5 is disposed between the innermost one of the second group of driving lines GTL2 and the sensor electrodes TE and RE to suppress mutual influence between the innermost one of the second group of driving lines GTL2 and the sensor electrodes TE and RE.

Figure 9:
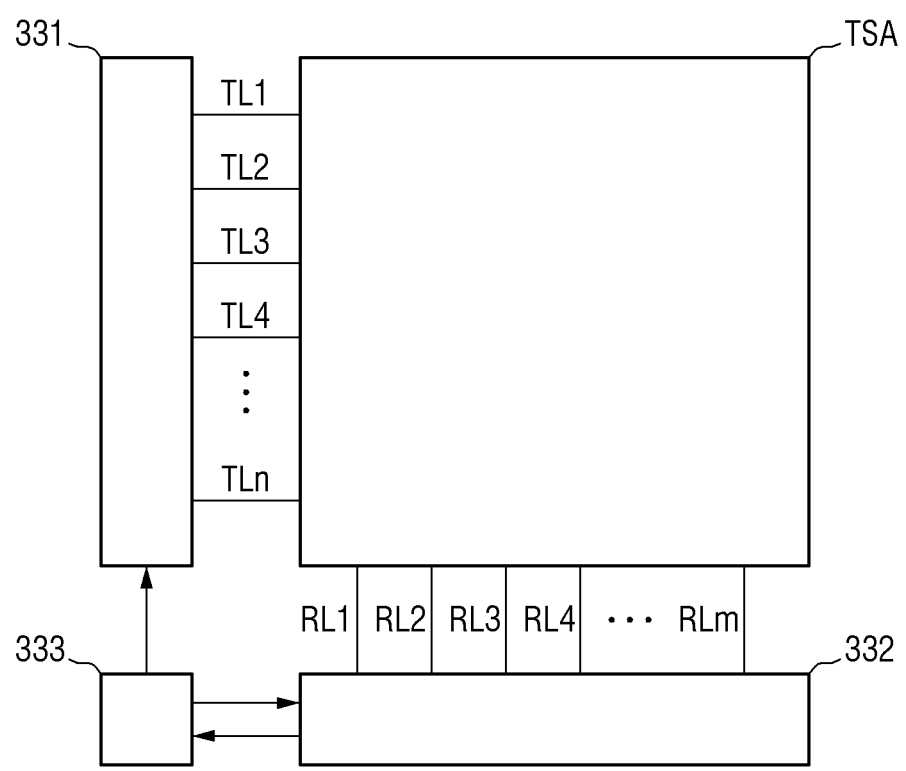
FIG. 9 is a block diagram showing the sensor unit of FIG. 8.

FIG. 9 is a block diagram of the sensor unit of FIG. 8 according to an exemplary embodiment. FIG. 9 exemplarily shows only the sensor area TSA and the sensor driver 330. The sensor driver 330 may include a driving signal output unit 331, a detector 332, and a sensor controller 333.

Figure 15:
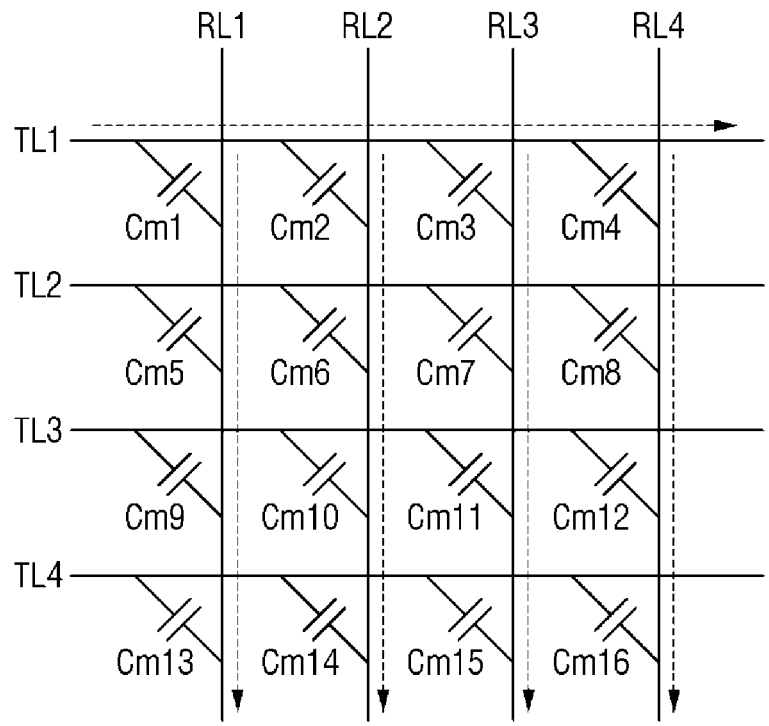
FIG. 15 is a view illustrating driving signals applied to driving lines in a second driving mode according to an exemplary embodiment.
Figure 16:
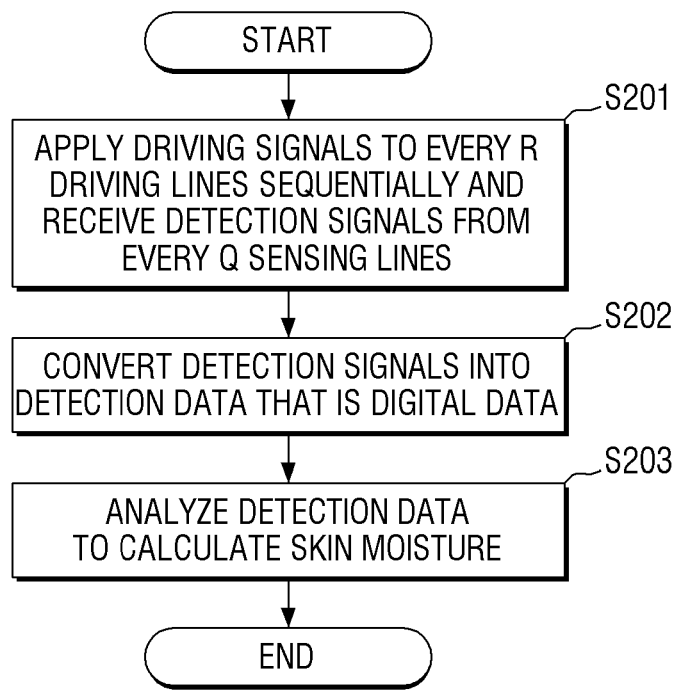
FIG. 16 is a flowchart for illustrating a touch sensing scheme by a sensor unit in a first driving mode according to an exemplary embodiment.

In addition, in FIGS. 9, 15 and 16, a $k^{th}$ driving line TLk refers to one of the second group of driving lines GTL2 or one of the first group of driving lines GTL1 connected to the driving electrodes disposed in the $k^{th}$ column of the sensor area TSA of FIG. 8, where $1 \le k \le n$. For example, in FIGS. 9, 15 and 16, a first driving line TL1 refers to one of the second group of driving lines GTL2 or one of the first group of driving lines GTL1 connected to the driving electrodes disposed in the first column of the sensor area TSA of FIG. 8. In FIG. 9, the $n^{th}$ driving line TLn refers to one of the second group of driving lines GTL2 or one of the first group of driving lines GTL1 connected to the driving electrodes disposed in the $n^{th}$ column of the sensor area TSA of FIG. 8. The driving electrodes arranged in the first column of the sensor area TSA may be the driving electrodes arranged in the leftmost column of the sensor area TSA, and the driving electrodes arranged in the second column of the sensor area TSA may be the driving electrodes arranged in the rightmost column of the sensor area TSA.

Referring to FIG. 9, the driving signal output unit 331 outputs driving signals to the driving lines TL1 to TLn under the control of the sensor controller 333. The driving signal output unit 331 may select driving lines to output the driving signals from the driving lines TL1 to TLn, and may output the driving signals to the selected driving lines.

In the second driving mode, the driving signal output unit 331 applies driving signals to the first R driving lines, then to the second R driving lines, and so on, where R is a positive integer less than P. The mutual capacitance(s) formed at the intersection(s) of the R driving electrodes and S sensing electrodes may be defined as a first unit sensor, where S is a positive integer less than Q.

For example, the driving signal output unit 331 may sequentially apply driving signals to the driving lines one-by-one in the second driving mode, as shown in FIG. 15. The driving signal output unit 331 may apply a driving signal to a first driving line TL1, then a driving signal to a first driving line TL2, then a driving signal to a first driving line TL3, and then a driving signal to a first driving line TL4. In this case, the unit sensor may include one mutual capacitance formed at the intersection of one driving line and one sensing line. One mutual capacitance formed at the intersection of one driving electrode and one sensing electrode may be defined as a "first unit sensor".

In this first driving mode, the driving signal output unit 331 applies driving signals to the first P driving lines, then to the second P driving lines, and so on, where P is a positive integer. The mutual capacitance(s) formed at the intersection(s) of the P driving electrodes and Q sensing electrodes may be defined as a second unit sensor. P may or may not be equal to Q.

Figure 17:
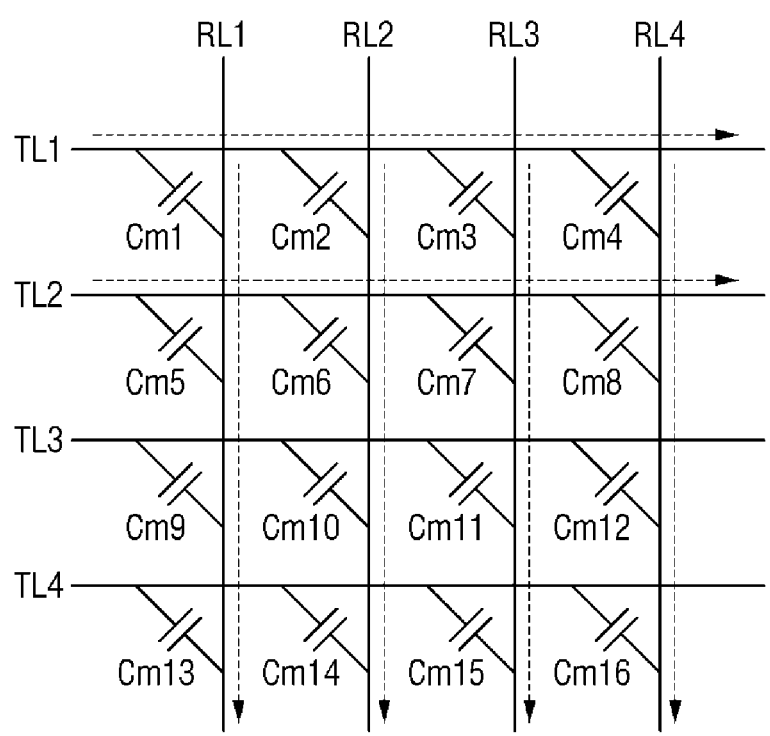
FIG. 17 is a view illustrating driving signals applied to driving lines in a first driving mode according to an exemplary embodiment.

For example, the driving signal output unit 331 may sequentially apply driving signals to the driving lines two-by-two in the first driving mode, as shown in FIG. 17. The driving signal output unit 331 may apply a driving signal to the first driving line TL1 and the second driving line TL2 simultaneously, and then may apply a driving signal to the third driving line TL3 and the fourth driving line TL4 simultaneously. In this case, the unit sensor may include one mutual capacitance formed at the intersection of two driving lines and two sensing lines. Four mutual capacitances formed at the intersections of the two driving electrodes and the two sensing electrodes may be defined as a "second unit sensor".

The detector 332 receives voltages charged in the mutual capacitances of the sensor electrodes through the sensing lines under the control of the sensor controller 333. The detector 332 converts the voltages charged in the mutual capacitances of the sensor electrodes received through the sensing lines into the detection data DD, which is digital data. The detector 332 may output the detection data DD to the main processor 710.

The sensor controller 333 may output a driving signal control signal VCS for setting the first driving lines TL1 and the second driving lines TL2, to which the driving signal is to be output, to the driving signal output unit 331. The sensor controller 333 may output a sensing control signal DCS to the detector 332 to notify the reception timing of amounts of change in the mutual capacitances of the sensor electrodes.

The main processor 710 receives the detection data DD from the detector 332. The main processor 710 may analyze the detection data DD and calculate changes in the mutual capacitances in the second driving mode. The main processor 710 may calculate a user's touch coordinates according to the amounts of change in the capacitance, and then execute an application indicated by the icon touched by the user or perform the operation. For example, when the amount of change in the mutual capacitance of a first unit sensor is greater than a first threshold value, the main processor 710 sets the coordinates of the first unit sensor as the coordinates of a user's touch in the second driving mode. For example, the main processor 710 may control the display device 10 so that an application corresponding to an icon displayed on touch coordinates is executed.

The main processor 710 receives the detection data DD from the detector 332. The main processor 710 may determine the user's skin moisture by analyzing the detection data DD in the first driving mode. For example, the main processor 710 may calculate the amounts of change in mutual capacitances of the second unit sensors according to the detection data DD. The main processor 710 may calculate a representative value obtained by adding up the amounts of change in the mutual capacitances of the second unit sensors. The main processor 710 may include a first look-up table that stores moisture data including information on a user's skin moisture associated with the representative value. When the main processor 710 outputs a representative value to the first look-up table, the main processor 710 may receive moisture data associated with the representative value from the first look-up table. The main processor 710 may control the display device 10 so that information on a user's skin moisture is displayed according to the moisture data.

Figure 10:
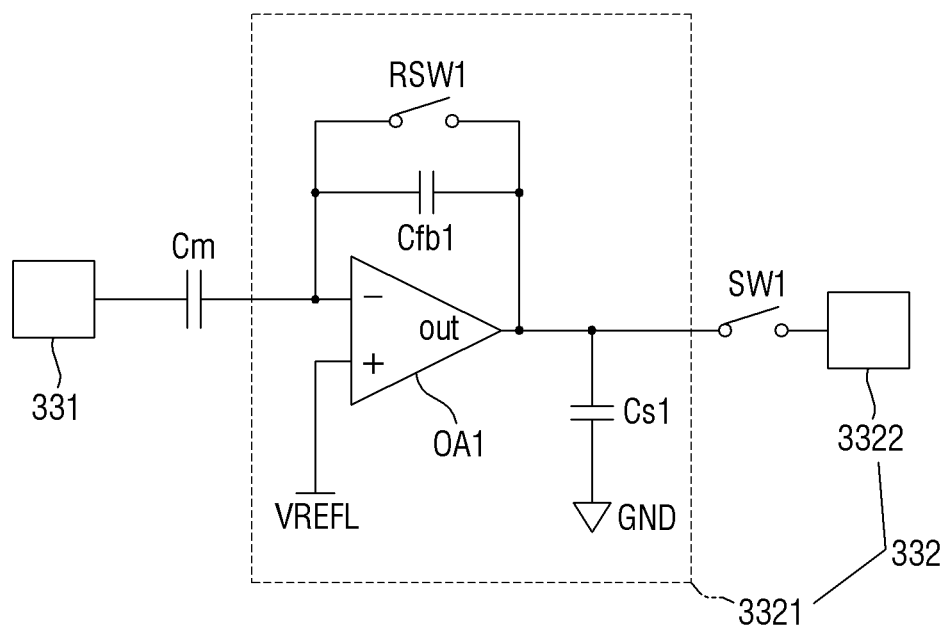
FIG. 10 is a diagram of a first driving electrode, a first sensing electrode, a driving signal output unit, and a detector for mutual capacitance sensing according to an exemplary embodiment.

FIG. 10 is a circuit diagram of a first driving electrode, a first sensing electrode, a driving signal output unit, and a detector for mutual capacitance sensing according to an exemplary embodiment. FIG. 10 exemplarily shows only one mutual capacitance Cm formed between one of the driving electrodes TE connected to the driving lines, and one of the sensing electrodes connected to the sensing lines.

Referring to FIG. 10, a touch driving circuit 400 may include a driving signal output unit 331 and a detector 332. The detector 332 may include a voltage detector 3321 and an analog-to-digital converter 3322.

The driving signal output unit 331 outputs a driving signal to a driving electrode through a driving line. The driving signal may include a plurality of pulses.

The voltage detector 3331 detects the voltage charged in the mutual capacitance through the sense line. The voltage detector 3321 may include an operational amplifier OA1, a feedback capacitor $C_{fb1}$, and a reset switch $R_{SW1}$. The operational amplifier OA1 may include a first input terminal (−), a second input terminal (+), and an output terminal (out). The first input terminal (−) of the operational amplifier OA1 may be connected to a first sense line RL1, the second input terminal (+) may be connected to an initialization voltage line $V_{REFL}$, from which an initialization voltage is supplied, and the output terminal (out) may be connected to the storage capacitor Cs1. The first storage capacitor Cs1 is connected between the output terminal (out) and the ground to store the output voltage Vout1 from the operational amplifier OA1. The feedback capacitor $C_{fb1}$ and the reset switch $R_{SW1}$ may be connected in parallel between the first input terminal (−) and the output terminal (out) of the operational amplifier OA1. The reset switch $R_{SW1}$ controls the connection between both ends of the feedback capacitor $C_{fb1}$. When the reset switch $R_{SW1}$ is turned on, such that both ends of the feedback capacitor $C_{fb1}$ are connected, the feedback capacitor $C_{fb1}$ may be reset.

The output voltage Vout1 from the operational amplifier OA1 may be defined as in Equation 1 below:

$$Vout1 = \frac{Vcm \times Vt1}{Cfb1} \quad \text{[Equation 1]}$$

In this case, Vout1 denotes the output voltage from the operational amplifier OA1, Vcm denotes the mutual capacitance, $C_{fb1}$ denotes the capacitance of the feedback capacitor $C_{fb1}$, and Vt1 denotes the voltage charged in the mutual capacitance Cm.

The analog-to-digital converter 3322 may be connected to the storage capacitor Cs1 through a switch SW1. The switch SW1 controls the connection between the analog-to-digital converter 3322 and the storage capacitor Cs1. Since the analog-to-digital converter 3322 is connected to the storage capacitor Cs1 when the switch SW1 is turned on, the analog-to-digital converter 3322 may convert the output voltage Vout1 stored in the storage capacitor Cs1 into digital data, and output the digital data.

Figure 11:
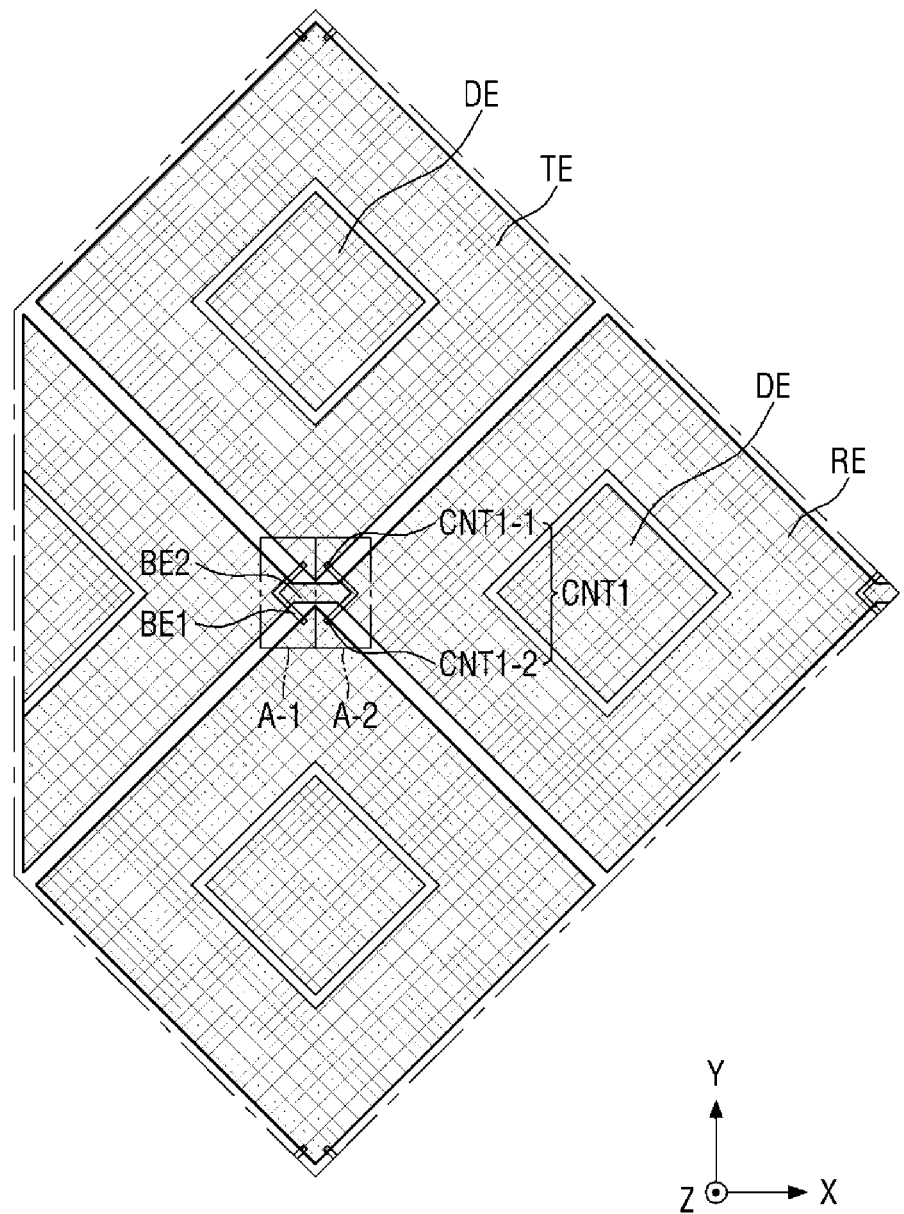
FIG. 11 is an enlarged plan view of area A of FIG. 8 according to an exemplary embodiment.

FIG. 11 is an enlarged plan view of area A of FIG. 8 according to an exemplary embodiment.

Referring to FIG. 11, the sensing electrodes RE may be arranged in the first direction (e.g., x-axis direction) and electrically connected to one another. The driving electrodes TE may be arranged in the second direction (e.g., y-axis direction) and electrically connected to one another. The conductive patterns DE may be surrounded by the driving electrodes TE and the sensing electrodes RE, respectively.

The driving electrodes TE, the sensing electrodes RE, and the conductive patterns DE may be electrically separated from each other. The driving electrodes TE, the sensing electrodes RE, and the conductive patterns DE may be disposed apart from each other.

As shown in FIG. 10, the driving electrodes TE and the sensing electrodes RE may have substantially the same size. The size of the driving electrodes TE may be greater than that of the conductive patterns DE. The size of the sensing electrodes RE may be greater than that of the conductive patterns DE. Although each of the driving electrodes TE, the sensing electrodes RE, and the conductive patterns DE has a diamond shape when viewed from the top in FIG. 10, however, the inventive concepts are not limited thereto, and the shape of each of the driving electrodes TE, the sensing electrodes RE, and the conductive patterns DE may be varied.

In order to electrically separate the sensing electrodes RE from the driving electrodes TE at their intersections, the driving electrodes TE adjacent to each other in the second direction (e.g., y-axis direction) may be connected through the first connection portions BE1, and the sensing electrodes RE adjacent to each other in the first direction (e.g., x-axis direction) may be connected through second connection portions BE2.

Figure 13:
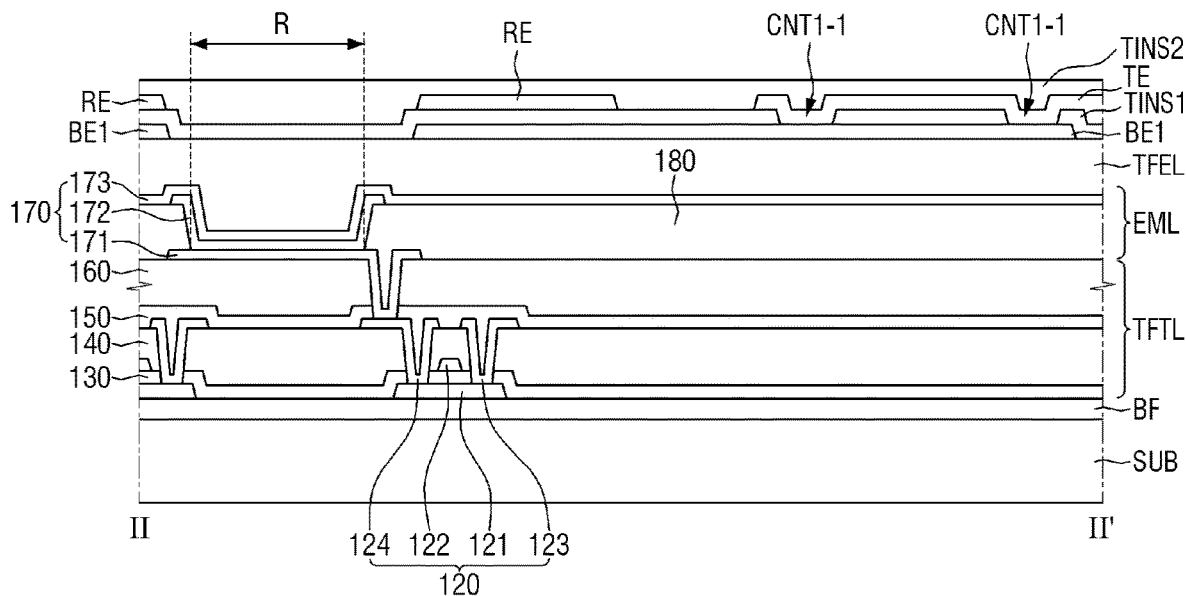
FIG. 13 is a cross-sectional view taken along line II-II' of FIG. 12.

The first connection portion BE1 may be formed on a different layer from the driving electrodes TE, and may be connected to the driving electrodes TE through the first contact holes CNT1. For example, the first connection portion BE1 may be formed in the first sensor electrode layer TSL1, as shown in FIG. 13, and the driving electrodes TE may be formed in the second sensor electrode layer TSL2, as shown in FIG. 13. The second sensor electrode layer TSL2 may be disposed on the first sensor electrode layer TSL1.

Each of the first connection portions BE1 may be bent at least once. In FIG. 11, the first connection portions BE1 are bent in the shape of "<" or ">", but the shape of the first connection portions BE1 is not limited thereto. In addition, since the driving electrodes TE adjacent to each other in the second direction (e.g., y-axis direction) are connected by the plurality of first connection portions BE1, even if any of the first connection portions BE1 is disconnected, the driving electrodes TE can still be stably connected with each other. Although two adjacent ones of the driving electrodes TE are illustrated as being connected by two first connection portions BE1 in FIG. 11, however, the inventive concepts are not limited thereto, and the number of first connection portions BE1 between adjacent driving electrodes TE may be varied.

Figure 14:
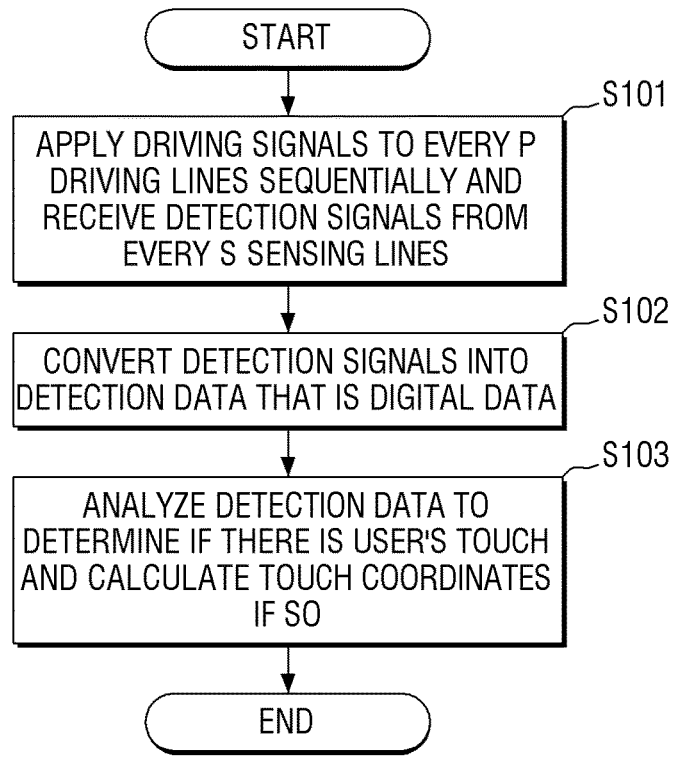
FIG. 14 is a flowchart for illustrating a touch sensing scheme by a sensor unit in a second driving mode according to an exemplary embodiment.

The second connection portion BE2 is formed on the same layer as the sensing electrodes RE, and may have a shape extended from the sensing electrodes RE. The sensing electrodes RE and the second connection portion BE2 may be formed of substantially the same material. For example, the sensing electrodes RE and the second connection portion BE2 may be formed in the second sensor electrode layer TSL2, as shown in FIG. 14.

According to the illustrated exemplary embodiment shown in FIG. 10, the first connection portions BE1 connecting the driving electrodes TE adjacent to each other in the second direction (e.g., y-axis direction) may be formed in the first sensor electrode layer TSL1, while the driving electrodes TE, the sensing electrodes RE, the conductive patterns DE, and the second connection portions BE2 may be formed in the second sensor electrode layer TSL2 different from the first sensor electrode layer TSL1. As such, the driving electrodes TE and the sensing electrodes RE may be electrically separated from each other at their intersections, while the sensing electrodes RE may be electrically connected with one another in the first direction (e.g., x-axis direction), and the driving electrodes TE may be electrically connected with each other in the second direction (e.g., y-axis direction).

Figure 12:
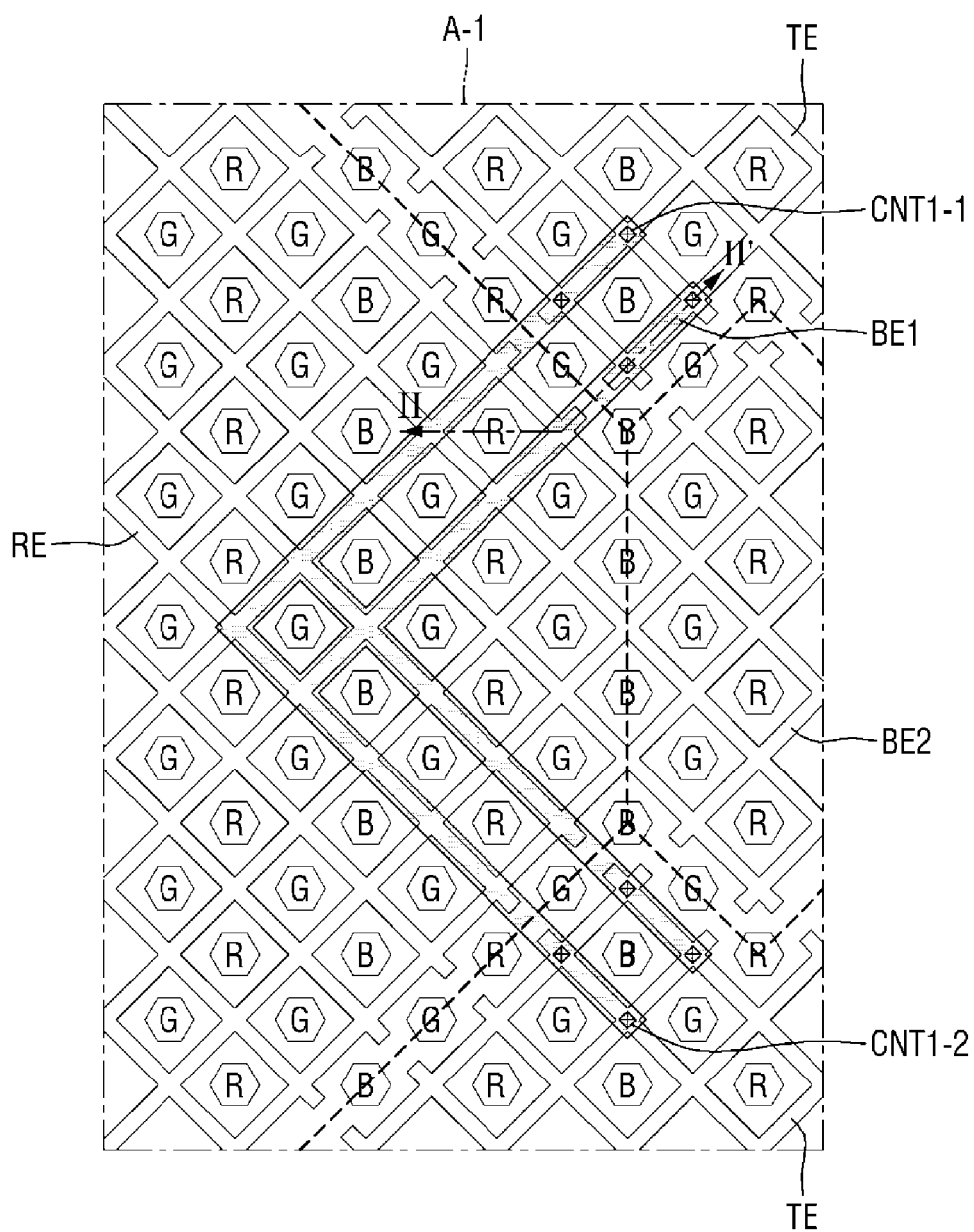
FIG. 12 is an enlarged plan view of area A-1 of FIG. 11 according to an exemplary embodiment.

FIG. 12 is an enlarged plan view of area A-1 of FIG. 11 according to an exemplary embodiment.

Referring to FIG. 12, the driving electrodes TE, the sensing electrodes RE, the first connection portions BE1, and the second connection portions BE2 may be formed in a mesh pattern. The conductive patterns DE may also be formed in a mesh pattern. When the sensor electrode layer SEL including the driving electrodes TE and the sensing electrodes RE is formed directly on the thin-film encapsulation layer TFEL as shown in FIG. 5, the distance between the second electrode of the emission material layer EML and each of the driving electrodes TE and the sensing electrodes RE of the layer TSL may become close. As such, a very large parasitic capacitance may be formed between the second electrode of the emission material layer EML and the driving electrodes TE and the sensing electrodes RE of the sensor electrode light source SEL, because the parasitic capacitance is proportional to the area, where the second electrode of the emission material layer EML overlaps with each of the driving electrodes TE and the sensing electrodes RE of the sensing electrode layer SEL. As such, in order to reduce the parasitic capacitance, each of the driving electrodes TE and the sensing electrodes RE may be formed in a mesh pattern.

The driving electrodes TE, the sensing electrodes RE, the conductive patterns DE, and the second connection portions BE2 are formed on the same layer and may be spaced apart from each other. There may be a gap between the driving electrode TE and the sensing electrode RE, between the driving electrode TE and the second connection portion BE2, between the driving electrode TE and the conductive pattern DE, and between the sensing electrode RE and the conductive pattern DE. In FIG. 12, the boundary between the driving electrode TE and the sensing electrode RE, and the boundary between the driving electrode TE and the second connection portion BE2 are indicated by dashed lines.

The first connection portions BE1 may be connected to the driving electrodes TE through the first contact holes CNT1, respectively. One end of each of the first connection portions BE1 may be connected to one of the driving electrodes TE adjacent to each other in the second direction (e.g., y-axis direction) through a first contact hole CNT1. The other end of each of the first connection portions BE1 may be connected to another one of the driving electrodes TE adjacent to each other in the second direction (e.g., y-axis direction) through a second contact hole CNT2. The first connection portions BE1 may overlap the driving electrodes TE and the sensing electrode RE. Alternatively, the first connection portion BE1 may overlap the second connection portion BE2 instead of the sensing electrode RE. Still alternatively, the first connection portion BE1 may overlap the sensing electrode RE as well as the second connection portion BE2. Since the first connection portion BE1 is formed on a different layer from the driving electrodes TE, the sensing electrodes RE, and the second connection portion BE2, a short-circuit may be prevented in the sensing electrode RE and/or the second connection portion BE2 even when the first connection portion BE1 overlaps the sensing electrode RE and/or the second connection portion BE2.

The second connection portion BE2 may be disposed between the sensing electrodes RE. The second connection portion BE2 is formed on the same layer as the sensing electrodes RE, and may be extended from each of the sensing electrodes RE. As such, the second connection portion BE2 may be connected to the sensing electrodes RE without a separate contact hole.

Sub-pixels R, G, and B may include a first sub-pixel R emitting a first color, a second sub-pixel G emitting a second color, and a third sub-pixel B emitting a third color. Although the first sub-pixel R is illustrated as a red sub-pixel, the second sub-pixel G is illustrated as a green sub-pixel, and the third sub-pixel B is illustrated as a blue sub-pixel in FIG. 12, however, the inventive concepts are not limited thereto. In addition, although the first sub-pixel R, the second sub-pixel G and the third sub-pixel B are illustrated as having a hexagonal shape when viewed from the top in FIG. 12, the inventive concepts are not limited thereto. For example, in some exemplary embodiments, the first sub-pixel R, the second sub-pixel G, and the third sub-pixel B may have a polygonal shape other than a hexagon, or a circular or elliptical shape when viewed from the top. In addition, while each the first sub-pixel R, the second sub-pixel G, and the third sub-pixel B is illustrated as having substantially the same size in FIG. 12, however, the inventive concepts are not limited thereto. For example, in some exemplary embodiments, the third sub-pixel B may have the largest size and the second sub-pixel G may have the smallest size. Alternatively, the size of the first sub-pixel R may be substantially equal to the size of the third sub-pixel B, and the size of the second sub-pixel G may be less than the size of each of the first sub-pixel R and the third sub-pixel B.

A pixel P refers to a group of sub-pixels capable of representing grayscales. In the illustrated exemplary embodiment of FIG. 12, a pixel P includes a first sub-pixel R, two second sub-pixels G, and a third sub-pixel B. However, the inventive concepts are not limited thereto. For example, in some exemplary embodiments, a pixel P may include a first sub-pixel PX1, a second sub-pixel PX2, and a third sub-pixel PX3.

Since the driving electrodes TE, the sensing electrodes RE, the conductive patterns DE, the first connection portions BE1, and the second connection portions BE2 are formed in a mesh pattern, the sub-pixels R, G and B may not overlap the driving electrodes TE, the sensing electrodes RE, the conductive patterns DE, the first connection portions BE1, and the second connection portions BE2. Accordingly, it is possible to prevent a path of light output from the sub-pixels R, G, and B from being covered by the driving electrodes TE, the sensing electrodes RE, the conductive patterns DE, the first connection portions BE1, and the second connection portions BE2, which may reduce the luminance of light.

Area A-2 shown in FIG. 11 is substantially symmetrical to the area A-1, and thus, repeated descriptions of the area A-2 will be omitted.

FIG. 13 is a cross-sectional view taken along line II-II' of FIG. 12.

Referring to FIG. 13, a thin-film transistor layer TFTL is formed on the substrate SUB. The thin-film transistor layer TFTL includes thin-film transistors 120, a gate insulating layer 130, an interlayer dielectric layer 140, a protective layer 150, and a planarization layer 160.

A buffer film BF may be formed on a surface of the substrate SUB. The buffer film BF may be formed on one surface of the substrate SUB in order to protect the thin-film transistors 120 and organic emitting layer 172 of the light-emitting element layer EML from moisture, which is likely to permeate through the substrate SUB. The buffer film BF may be formed of a plurality of inorganic layers stacked one over another. For example, the buffer film BF may include one or more inorganic layers, such as a silicon nitride layer, a silicon oxynitride layer, a silicon oxide layer, a titanium oxide layer, and an aluminum oxide layer, which may be alternately stacked one over another. In some exemplary embodiments, the buffer film BF may be omitted.

The thin-film transistors 120 are disposed on the buffer film BF. Each of the thin-film transistor 120 includes an active layer 121, a gate electrode 122, a source electrode 123, and a drain electrode 124. In FIG. 14, the thin-film transistors 120 are implemented as top-gate transistors, in which the gate electrode 122 is located above the active layer 121. However, the inventive concepts are not limited thereto. For example, in some exemplary embodiments, the thin-film transistors 210 may be implemented as bottom-gate transistors, in which the gate electrode 122 is located below the active layer 121, or as double-gate transistors, in which the gate electrodes 122 are disposed above and below the active layer 121.

The active layer 121 is formed on the buffer layer BF. The active layer 121 may include polycrystalline silicon, single crystal silicon, low-temperature polycrystalline silicon, amorphous silicon, or an oxide semiconductor. The oxide semiconductor may include, for example, a binary compound (ABx), a ternary compound (ABxCy), and a quaternary compound (ABxCyDz) including indium, zinc, gallium, tin, titanium, aluminum, hafnium (Hf), zirconium (Zr), magnesium (Mg), etc. For example, the active layer 121 may include an oxide including indium, tin, and titanium (ITZO) or an oxide including indium, gallium and tin (IGZO). In some exemplary embodiments, a light-blocking layer for blocking external light incident on the active layer 121 may be formed between the buffer layer BF and the active layer 121.

The gate insulating layer 130 may be formed on the active layer 121. The gate insulating layer 130 may be formed of an inorganic layer, for example, a silicon nitride layer, a silicon oxynitride layer, a silicon oxide layer, a titanium oxide layer, or an aluminum oxide layer. In FIG. 14, the gate insulating layer 130 is illustrated as being formed on the entire buffer film BF irrespectively of the gate electrode 122, however, the inventive concepts are not limited thereto. For example, in some exemplary embodiments, the gate insulating layer 130 may be formed only over the gate electrode 122.

The gate electrodes 122 and gate lines may be formed on the gate insulating layer 130. The gate electrodes 122 and the gate lines may be made up of a single layer or multiple layers of one of molybdenum (Mo), aluminum (Al), chromium (Cr), gold (Au), titanium (Ti), nickel (Ni), neodymium (Nd), and copper (Cu), or an alloy thereof.

The interlayer dielectric layer 140 may be formed over the gate electrodes 122 and the gate lines. The interlayer dielectric layer 140 may be formed of an inorganic layer, for example, a silicon nitride layer, a silicon oxynitride layer, a silicon oxide layer, a titanium oxide layer, or an aluminum oxide layer.

The source electrodes 123 and the drain electrodes 124 may be formed on the interlayer dielectric layer 140. Each of the source electrodes 123 and the drain electrodes 124 may be connected to the active layer 121 through a contact hole penetrating through the gate insulating layer 130 and the interlayer dielectric layer 140. The source electrode 123 and the drain electrode may be made up of a single layer or multiple layers of one of molybdenum (Mo), aluminum (Al), chromium (Cr), gold (Au), titanium (Ti), nickel (Ni), neodymium (Nd), and copper (Cu), or an alloy thereof.

The protective layer 150 may be formed on the source electrode 213 and the drain electrode 124 in order to insulate the thin-film transistors 120. The protective layer 150 may be formed of an inorganic layer, for example, a silicon nitride layer, a silicon oxynitride layer, a silicon oxide layer, a titanium oxide layer, or an aluminum oxide layer.

The planarization layer 160 may be formed on the protective layer 150 to provide a flat surface over the step differences of the thin-film transistors 120. The planarization layer 160 may be formed of an organic layer, such as an acryl resin, an epoxy resin, a phenolic resin, a polyamide resin, and a polyimide resin.

The emission material layer EML is formed on the thin-film transistor layer TFTL. The emission material layer EML includes light-emitting elements 170 and a bank layer 180.

The light-emitting elements 170 and the bank layer 180 are formed on the planarization layer 160. Each of the light-emitting elements 170 may include a first electrode 171, an organic emitting layer 172, and a second electrode 173.

The first electrode 171 may be formed on the planarization layer 160. Although the first electrode 171 is illustrated as being connected to the drain electrode 124 of the thin-film transistor 120 through the contact hole penetrating through the protective layer 150 and the planarization layer 160 in FIG. 14, however, the inventive concepts are not limited thereto. The first electrode 171 may be connected to the source electrode 123 of the thin-film transistor 120 through the contact hole penetrating through the protective layer 150 and the planarization layer 160.

In the top-emission organic light-emitting diode emitting light from the organic emitting layer 172 toward the second electrode 173, the first electrode 171 may be made of a metal material having a high reflectivity, such as a stack structure of aluminum and titanium (Ti/Al/Ti), a stack structure of aluminum and ITO (ITO/Al/ITO), an APC alloy, and a stack structure of APC alloy and ITO (ITO/APC/ITO). The APC alloy may be an alloy of silver (Ag), palladium (Pd), and copper (Cu).

In the bottom-emission organic light-emitting diode emitting light from the organic emitting layer 172 toward the first electrode 171, the first electrode 171 may be formed of a transparent conductive material (TCP), such as ITO and IZO that can transmit light, or a semi-transmissive conductive material, such as magnesium (Mg), silver (Ag), and an alloy of magnesium (Mg) and silver (Ag). In this case, when the first electrode 171 is made of a semi-transmissive metal material, the light extraction efficiency can be increased by using microcavities.

The bank layer 180 may be formed to separate the first electrode 171 from one another on the planarization layer 250 in order to define the sub-pixels R, G, and B. The bank layer 180 may be formed to cover the edge of the first electrode 171. The bank layer 180 may be formed of an organic layer, such as an acryl resin, an epoxy resin, a phenolic resin, a polyamide resin, and a polyimide resin.

In each of the sub-pixels R, G, and B, the first electrode 171, the organic emitting layer 172, and the second electrode 173 are stacked one over another sequentially, so that holes from the first electrode 171 and electrons from the second electrode 173 may be combined with each other in the organic emitting layer 172 to emit light. The second sub-pixel G and the third sub-pixel B may be formed substantially the same as the first sub-pixel R shown in FIG. 13.

The organic emitting layer 172 is formed on the first electrode 171 and the bank layer 180. The organic emitting layer 172 may include an organic material and emit light of a certain color. For example, the organic emitting layer 172 may include a hole transporting layer, an organic material layer, and an electron transporting layer. In this case, the organic emitting layer 172 of the red sub-pixel R may emit red light, the organic emitting layer 172 of the green sub-pixel G may emit green light, and the organic emitting layer 172 of the blue sub-pixel B may emit blue light.

Alternatively, the organic emitting layers 172 of the sub-pixels R, G, and B may be formed as a single layer to emit white light, ultraviolet light, or blue light. In this case, the red sub-pixel R may overlap a red color filter layer transmitting red light, the green sub-pixel G may overlap a green color filter layer transmitting green light, and the blue sub-pixel B may overlap a blue color filter layer transmitting blue light. The red color filter layer, the green color filter layer, and the blue color filter layer may be disposed on the thin-film encapsulation layer TFEL. In addition, in other exemplary embodiments, the red sub-pixel R may overlap a red wavelength conversion layer that converts ultraviolet light or blue light into red light, the green sub-pixel G may overlap a green wavelength conversion layer that converts ultraviolet light or blue light into green light, and the blue sub-pixel B may overlap a blue wavelength conversion layer that converts ultraviolet light or blue light into blue light. The red wavelength conversion layer, the green wavelength conversion layer, and the blue wavelength conversion layer may be disposed on the thin-film encapsulation layer TFEL. For example, the red wavelength conversion layer may be disposed between the thin-film encapsulation layer TFEL and the red color filter layer, the green wavelength conversion layer may be disposed between the thin-film encapsulation layer TFEL and the green color filter layer, and the blue wavelength conversion layer may be disposed between the thin-film encapsulation layer TFEL and the blue color filter layer.

The second electrode 173 is formed on the organic emitting layer 172. The second electrode 173 may be formed to cover the organic emitting layer 172. The second electrode 173 may be a common layer formed across the pixels P. A capping layer may be formed on the second electrode 173.

In the top-emission organic light-emitting diode, the second electrode 173 may be formed of a transparent conductive material (TCP), such as ITO and IZO that can transmit light, or a semi-transmissive conductive material, such as magnesium (Mg), silver (Ag), and an alloy of magnesium (Mg) and silver (Ag). When the second electrode 173 is formed of a transflective metal material, the light extraction efficiency can be increased by using microcavities.

In the bottom-emission organic light-emitting diode, the second electrode 173 may be made of a metal material having a high reflectivity, such as a stack structure of aluminum and titanium (Ti/Al/Ti), a stack structure of aluminum and ITO (ITO/Al/ITO), an APC alloy, and a stack structure of APC alloy and ITO (ITO/APC/ITO). As described above, the APC alloy may be an alloy of silver (Ag), palladium (Pd), and copper (Cu).

The thin-film encapsulation layer TFFL is formed on the light-emitting element layer EML. The thin-film encapsulation layer TFEL is disposed on the second electrode 173. The thin-film encapsulation layer TFEL may include at least one inorganic layer to prevent oxygen or moisture from permeating into the organic emitting layer 172 and the second electrode 173. In addition, the thin-film encapsulation layer TFEL may include at least one organic layer to protect the emission material layer EML from particles, such as dust.

For example, the thin-film encapsulation layer TFEL may include a first inorganic layer disposed on the second electrode 173, an organic layer disposed on the first inorganic layer, and a second inorganic layer disposed on the organic layer. The first inorganic layer and the second inorganic layer may be formed of, but is not limited to, a silicon nitride layer, a silicon oxynitride layer, a silicon oxide layer, a titanium oxide layer, or an aluminum oxide layer. The organic layer may be formed of, but is not limited to, an acryl resin, an epoxy resin, a phenolic resin, a polyamide resin, and a polyimide resin.

The sensor electrode layer SEL is formed on the thin-film encapsulation layer TFEL. A buffer layer may be further formed between the thin-film encapsulation layer TFEL and the sensor electrode layer SEL. The sensor electrode layer SEL may include a first sensor electrode layer TSL1 and a second sensor electrode layer TSL2. FIG. 13 shows only the driving electrode TE, the sensing electrode RE, and the first connection portion BE1 of the sensor electrode layer SEL.

The first sensor electrode layer TSL1 is formed on the thin-film encapsulation layer TFEL. The first sensor electrode layer TSL1 may include first connection portions BE1. The first sensor electrode layer TSL1 may be made up of, but is not limited to, a stack structure of aluminum and titanium (Ti/Al/Ti), a stack structure of aluminum and ITO (ITO/Al/ITO), an APC alloy, and a stack structure of APC alloy and ITO (ITO/APC/ITO).

A first touch insulating layer TINS1 is formed on the first sensor electrode layer TSL1. The first touch insulating layer TINS1 may be formed of an inorganic layer, for example, a silicon nitride layer, a silicon oxynitride layer, a silicon oxide layer, a titanium oxide layer, or an aluminum oxide layer. Alternatively, the first touch insulating layer TINS1 may be formed of an organic layer, such as an acryl resin, an epoxy resin, a phenolic resin, a polyamide resin, and a polyimide resin.

The second sensor electrode layer TSL2 is formed on the first touch insulating layer TINS1. The second sensor electrode layer TSL2 may include the driving electrodes TE, the sensing electrodes RE, the conductive patterns DE, the first connection portions BE1, the second connection portions BE2, and the first group of driving lines GTL1, the second group of driving lines GTL2, the sensing lines RL, the guard lines GL1, GL2, GL3, GL4 and GL5, and the ground lines GRL1, GRL2, GRL3 and GRL4. The second sensor electrode layer TSL2 may be made up of, but is not limited to, a stack structure of aluminum and titanium (Ti/Al/Ti), a stack structure of aluminum and ITO (ITO/Al/ITO), an APC alloy, and a stack structure of APC alloy and ITO (ITO/APC/ITO).

First contact holes CNT1 may be formed through the first touch insulating layer TINS1, via which the first connection portions BE1 are exposed. The driving electrodes TE may be connected to the first connection portions BE1 through the first contact holes CNT1.

A second touch insulating layer TINS2 is formed on the second sensor electrode layer TSL2. The second touch insulating layer TINS2 may provide a flat surface over the level difference created by the first sensor electrode layer TSL1 and the second sensor electrode layer TSL2. The second touch insulating layer TINS2 may be formed of an organic layer, such as an acryl resin, an epoxy resin, a phenolic resin, a polyamide resin, and a polyimide resin.

According to the illustrated exemplary embodiment shown in FIG. 13, the first connection portions BE1 connecting the driving electrodes TE adjacent to each other in the second direction (e.g., y-axis direction) may be formed in the first sensor electrode layer TSL1, while the driving electrodes TE, the sensing electrodes RE, and the second connection portions BE2 may be formed in the second sensor electrode layer TSL2 different from the first sensor electrode layer TSL1. As such, the driving electrodes TE and the sensing electrodes RE may be electrically separated from each other at their intersections, while the sensing electrodes RE may be electrically connected with one another in the first direction (e.g., x-axis direction), and the driving electrodes TE and proximity sensing electrodes PE may be electrically connected with each other in the second direction (e.g., y-axis direction).

FIG. 14 is a flowchart for illustrating a touch sensing scheme by a sensor unit in a second driving mode according to an exemplary embodiment.

Referring to FIG. 14, the driving signal output unit 331 applies driving signals to the first R driving lines TL1 and TL2, to the second R driving lines, and so on. The detector 332 detects voltages charged in the mutual capacitances through the sensing lines RL, and converts the voltages charged in the mutual capacitances sensed by the first S sensing lines, by the second S sensing lines, and so on, into detection data, which may be digital data. As used herein, the voltage of the mutual capacitance detected by the detector 332 may be referred to as a detection signal (steps S101 and S102 of FIG. 14).

The driving signal output unit 331 applies driving signals to the first R driving lines TL1 to TL4, to the second R driving lines, and so on, according to the driving signal control signal VCS in the second driving mode. For example, as shown in FIG. 15, in the second driving mode, the driving signal output unit 331 may apply a driving signal to a first driving line TL1, then a driving signal to a first driving line TL2, then a driving signal to a first driving line TL3, and then a driving signal to a first driving line TL4.

The detector 332 detects the voltages charged in the mutual capacitances of every S sensing lines according to a sensing control signal DCS in the second driving mode. The detector 332 converts the detected voltages charged in the mutual capacities received through the sensing lines into the detection data DD, which is digital data. In this case, the mutual capacitance(s) formed at the intersection(s) of the R driving electrodes and S sensing electrodes may be defined as a first unit sensor. In particular, the voltage(s) charged in the R-by-S mutual capacitance(s) of a first unit sensor may be calculated as one detection data DD by the detector 332.

For example, the driving signal output unit 331 may sequentially apply driving signals to the driving lines one-by-one in the second driving mode as shown in FIG. 15. The detector 332 may detect the voltage charged in the mutual capacitances of the sensing lines one-by-one in the second driving mode. In this case, the mutual capacitance formed at the intersection of one driving electrode and one sensing electrode may be defined as a first unit sensor. In particular, the voltage charged in one mutual capacitance of a first unit sensor may be calculated as one detection data DD by the detector 332. In FIG. 15, each of the first to sixteenth mutual capacitances $C_{m1}$ to $C_{m16}$ may be defined as one unit sensor.

Then, the detection data DD is analyzed to determine whether there is a user's touch (step S103 of FIG. 14).

The main processor 710 receives the detection data DD from the detector 332. The main processor 710 may analyze the detection data DD and calculate changes in the mutual capacities in the second driving mode. The main processor 710 may calculate a user's touch coordinates according to the amounts of change in the mutual capacitances, and then execute an application indicated by the icon touched by the user or perform the operation. For example, when the amount of change in the mutual capacitance of a first unit sensor calculated based on the detection data DD is greater than a first threshold value, the main processor 710 sets the coordinates of the first unit sensor as the coordinates of a user's touch in the second driving mode. For example, the main processor 710 may control the display device 10 so that an application indicated by an icon displayed on touch coordinates is executed.

FIG. 16 is a flowchart for illustrating a touch sensing scheme by a sensor unit in a first driving mode according to an exemplary embodiment.

Referring to FIG. 16, the driving signal output unit 331 applies driving signals to every P driving lines TL1 and TL2. The detector 332 detects voltages charged in the mutual capacitances of every Q sensing lines through the sensing lines RL, and converts the voltages charged in the mutual capacitances into detection data, which may be digital data. As used herein, the voltage of the mutual capacitance detected by the detector 332 may be referred to as a detection signal (steps S201 and S202 of FIG. 16).

The driving signal output unit 331 applies driving signals to every P driving lines TL1 to TL2 according to the driving signal control signal VCS in the first driving mode. For example, in the first driving mode, the driving signal output unit 331 may apply a driving signal to the first driving line TL1 and the second driving line TL2 simultaneously, and then may apply a driving signal to the third driving line TL3 and the fourth driving line TL4 simultaneously.

The detector 332 detects the voltages charged in the mutual capacitances of every Q sensing lines according to a sensing control signal DCS in the first driving mode. The detector 332 converts the detected voltages charged in the mutual capacities received through the sensing lines into the detection data DD, which may be digital data. In this case, the mutual capacitance(s) formed at the intersection(s) of the P driving electrodes and Q sensing electrodes may be defined as a second unit sensor. In particular, the amounts of change(s) in the P-by-Q mutual capacitance(s) of a second unit sensor may be calculated as one detection data DD by the detector 332.

When the mutual capacitances of the second unit sensor has a greater value, the amounts of change in the mutual capacitances of the second unit sensor may also have a greater value according to a person's skin moisture. As such, the mutual capacitances of the second unit sensor may be greater than that of the first unit sensor. Accordingly, the detection data DD calculated by the mutual capacitances of the second unit sensor may be greater than the detection data DD calculated by the mutual capacitances of the first unit sensor.

For example, the driving signal output unit 331 may sequentially apply driving signals to the driving lines two-by-two in the first driving mode, as shown in FIG. 17. The detector 332 may receive the amounts of change in the mutual capacitances of every two sensing lines in the first driving mode. In this case, the mutual capacitance formed at the intersections of the two driving electrodes and the two sensing electrodes may be defined as a second unit sensor. In particular, the amounts of change in four mutual capacitances of a second unit sensor may be calculated as one detection data DD by the detector 332.

Then, the detection data DD is analyzed to calculate the user's skin moisture (step S204 of FIG. 16).

The main processor 710 receives the detection data DD from the detector 332. The main processor 710 may determine the user's skin moisture by analyzing the detection data DD in the first driving mode. For example, the main processor 710 may calculate the amounts of change in mutual capacitances of the second unit sensors according to the detection data DD. The main processor 710 may calculate a representative value obtained by adding up the amounts of change in the mutual capacitances of the second unit sensors. The main processor 710 may include a first look-up table that stores moisture data including information on a user's skin moisture associated with the representative value. When the main processor 710 outputs a representative value to the first look-up table, the main processor 710 may receive moisture data associated with the representative value from the first look-up table. The main processor 710 may control the display device 10 so that information on a user's skin moisture is displayed according to the moisture data.

According to the illustrated exemplary embodiment shown in FIG. 16, the number of mutual capacitances of the second unit sensor in the first driving mode is greater than the number of mutual capacitances of the first unit sensor in the second driving mode, so that the mutual capacitances of the second unit sensor can be greater than the mutual capacitances of the first unit sensor. In this manner, the difference between the amounts of change in mutual capacitances of the second unit sensor may become larger according to a person's skin moisture, so that the skin moisture can be measured.

Figure 18:
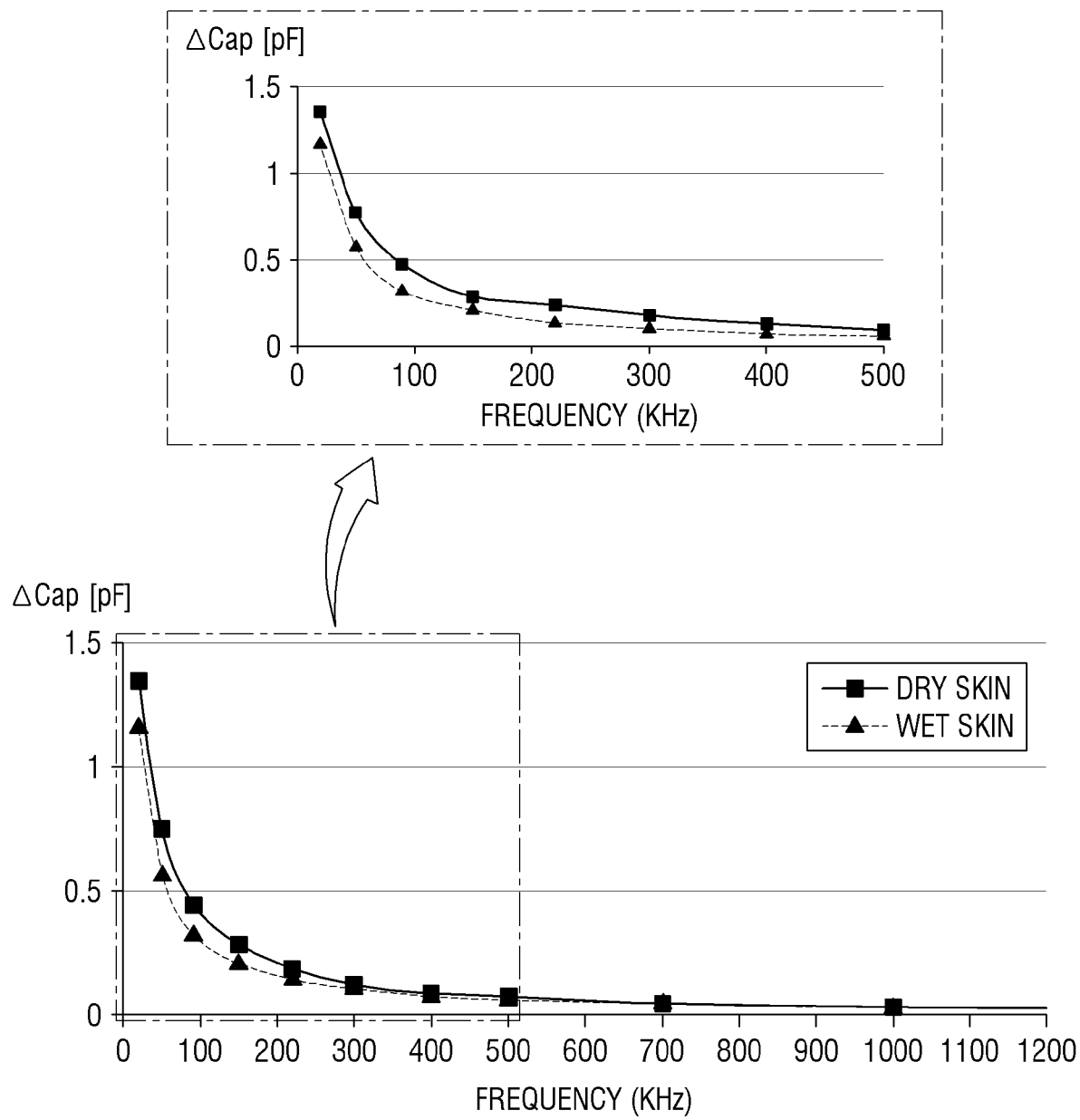
FIG. 18 is a graph showing the amount of change in the total mutual capacitance according to the frequency of the driving signal in the first driving mode.

FIG. 18 is a graph showing the amount of change in the total mutual capacitance according to the frequency of the driving signal in the first driving mode.

In the graph shown in FIG. 18, the x-axis represents the frequency (kHz) of the driving signal, and the y-axis represents the representative value $\Delta C_{ap}$ calculated based on the detection data DD. The representative value may be the sum of amounts of change in the mutual capacitances of the second unit sensors.

Referring to FIG. 18, when the frequency of the driving signal ranges from about 50 kHz to about 500 kHz in the first driving mode, there may be a difference in the representative value $\Delta C_{ap}$ between a dry skin and a wet skin. On the other hand, when the frequency of the driving signal is greater than about 500 kHz, there is almost no difference in the representative value $\Delta C_{ap}$ between the dry skin and the wet skin. As such, the frequency of the driving signal output from the driving signal output unit 331 in the first driving mode may range from about 50 kHz to about 500 kHz.

The driving signal output unit 331 may output the driving signal at a first frequency in the second driving mode, and may output the driving signal at a second frequency in the first driving mode. For example, the first frequency may be about 200 kHz, and the second frequency may be about 50 kHz to about 500 kHz.

Since the first frequency is in the range of the second frequency, the driving signal output unit 331 may output the driving signal at the same frequency in the second driving mode and the first driving mode in order to simplify the driving method.

In addition, the difference in the representative value $\Delta C_{ap}$ between the dry skin and the wet skin is larger when the second frequency is about 50 kHz to about 100 kHz than when the second frequency is about 100 kHz to about 500 kHz. As such, in order to increase the accuracy in measuring the skin moisture, the driving signal output unit 331 may output the driving signal at a frequency of about 50 kHz to about 500 kHz in the first driving mode. In this case, the driving signal output unit 331 may output the driving signals at different frequencies between the second driving mode and the first driving mode.

Figure 19:
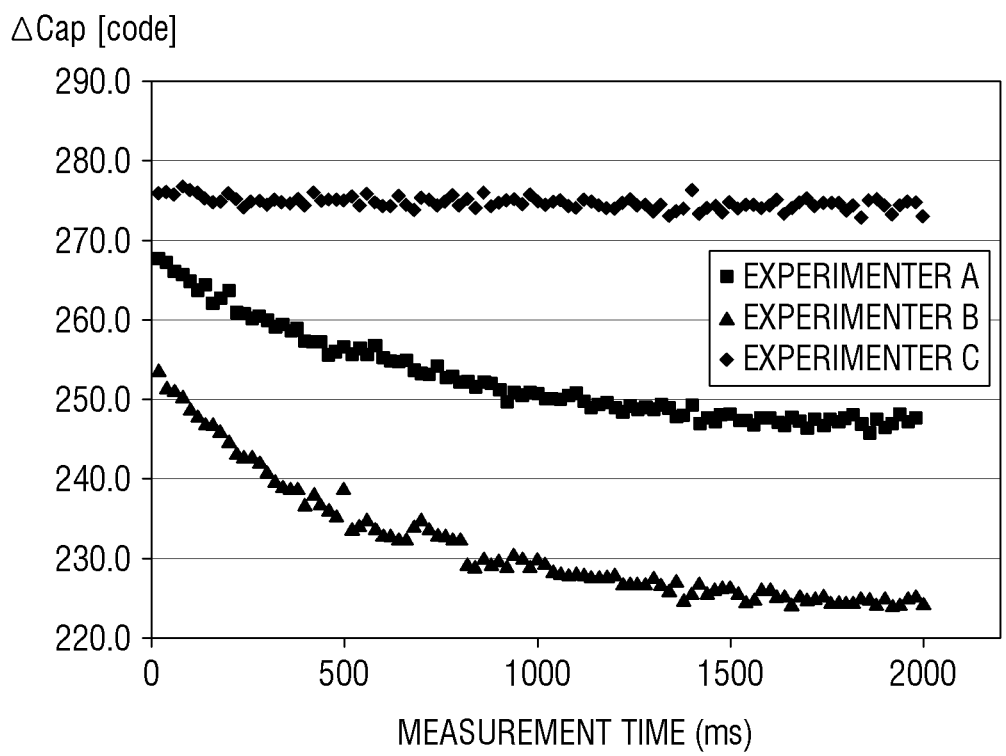
FIG. 19 is a graph showing the amounts of change in the total mutual capacitances over time for different experimenters in the first driving mode.

FIG. 19 is a graph showing the amounts of change in the total mutual capacitances over time for different experimenters in the first driving mode.

In the graph shown in FIG. 19, the x-axis represents the frequency (kHz) of the driving signal, and the y-axis represents the representative value $\Delta C_{ap}$ calculated based on the detection data DD. The representative value may be the sum of amounts of change in the mutual capacitances of the second unit sensors.

Referring to FIG. 19, there may be differences in time period until the representative value $\Delta C_{ap}$ is saturated depending on the persons' skins. For example, in the experimenter A, the representative value $\Delta C_{ap}$ is hardly changed, whereas for the experimenter B and the experimenter C, the representative value $\Delta C_{ap}$ may be saturated after approximately 1,500 ms, i.e., about 1.5 seconds.

The time period until the representative value $\Delta C_{ap}$ is saturated at 90% may be approximately 1,000 ms, that is, approximately 1 second. Even when the representative value $\Delta C_{ap}$ is saturated at 90%, the skin moisture can be calculated based on the representative value $\Delta C_{ap}$. Therefore, the time period, during which the driving signal is applied in the first driving mode, may be approximately 1 second to 1.5 seconds. Accordingly, the driving signal output unit 311, in the first driving mode, may sequentially apply driving signals to the first P driving lines, to the second P driving lines, and so on, for approximately 1 second or 1.5 second repeatedly. As such, the time period in which the driving signals are sequentially applied to the first P driving lines, to the second P driving lines, and so on in the first driving mode may be longer than the time period in which the driving signals are sequentially applied to the first R driving lines, to the second R driving lines, and so on in the second driving mode.

Figure 20:
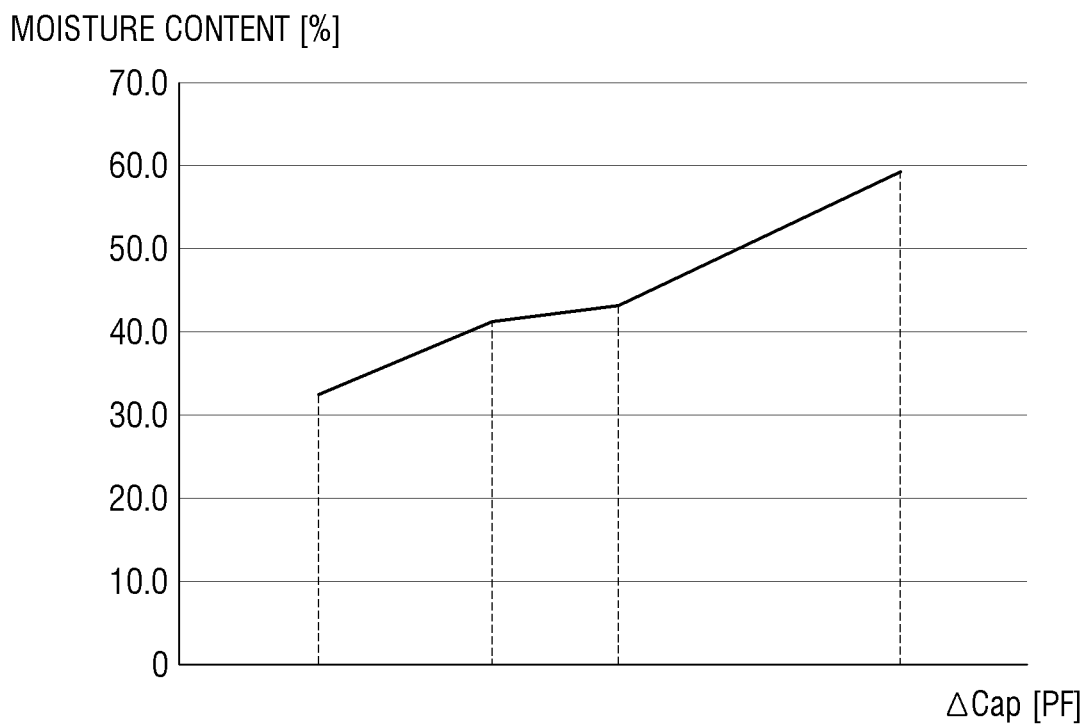
FIG. 20 is a graph showing skin moisture content versus capacitance of total mutual capacitance.

FIG. 20 is a graph showing skin moisture content versus capacitance of total mutual capacitance.

In the graph shown in FIG. 20, the x-axis represents the representative value $\Delta C_{ap}$, and the y-axis represents the skin moisture content (%). The skin moisture content may be expressed from 0 to 100%. The representative value may be the sum of amounts of change in mutual capacitances of the second unit sensors.

Referring to FIG. 20, the representative value $\Delta C_{ap}$ is proportional to the skin moisture content. In particular, the larger the representative value $\Delta C_{ap}$ is, the higher the skin moisture content is, and vice versa.

Figure 21:
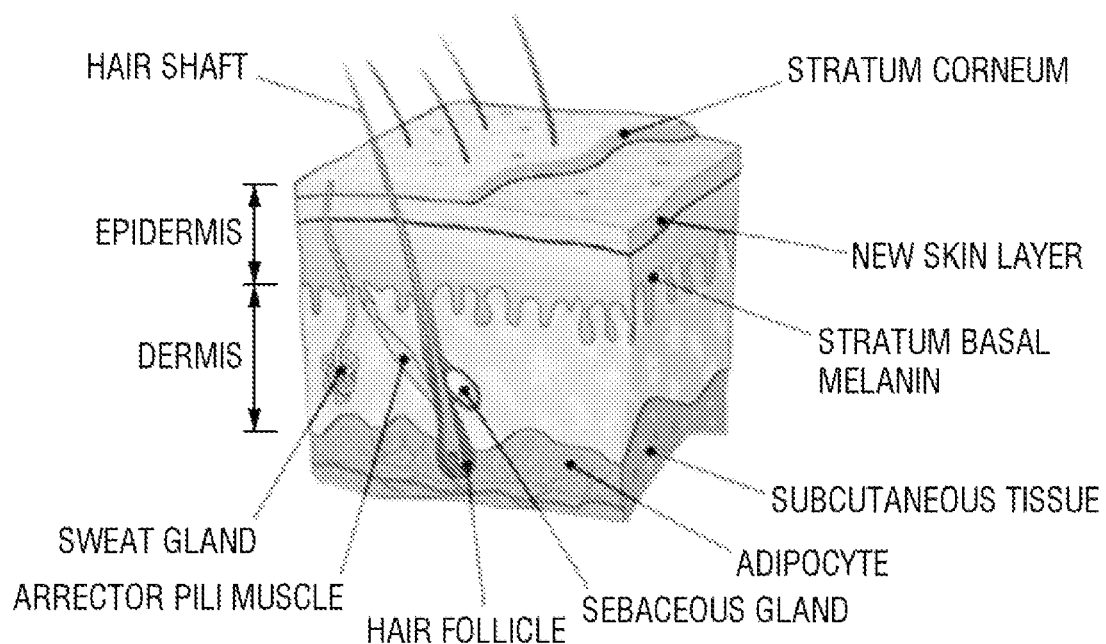
FIG. 21 is an exemplary view of a human skin structure.
Figure 22:
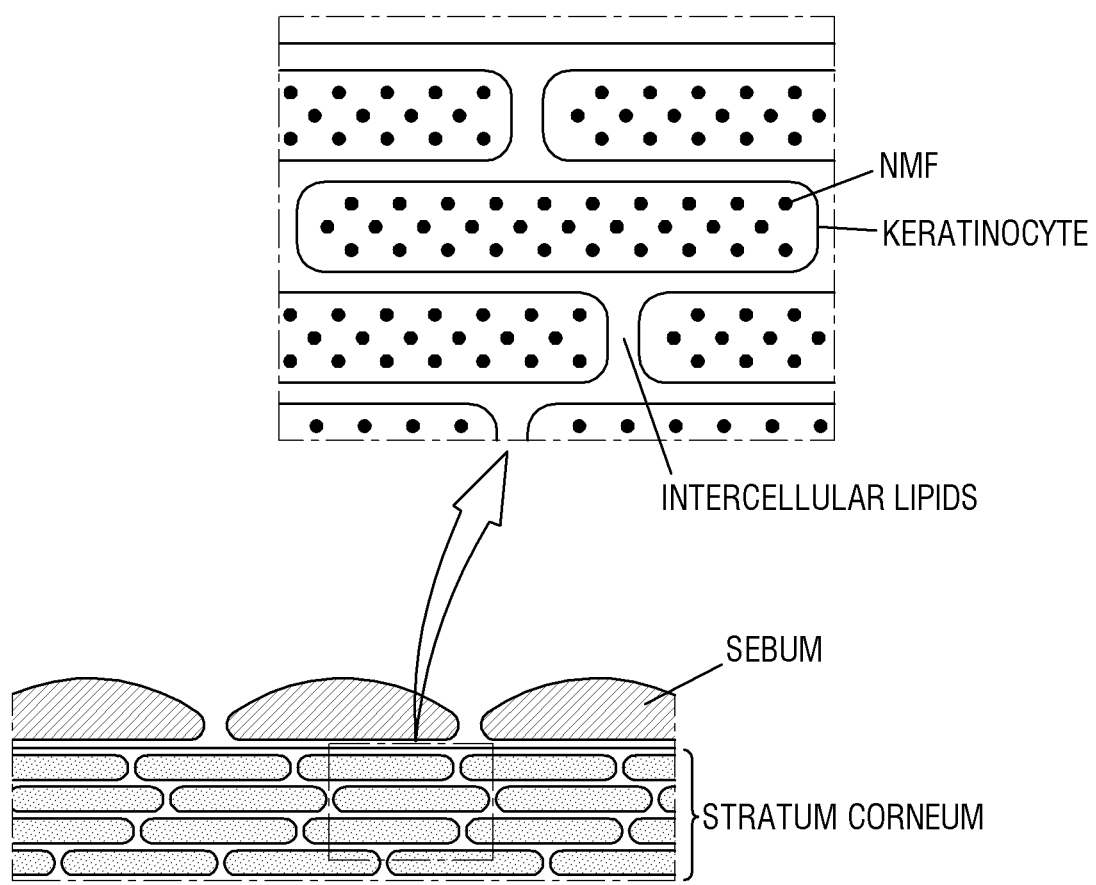
FIG. 22 is an enlarged view of the stratum corneum shown in FIG. 21.

Human skin includes the stratum corneum, epidermis, and dermis, as shown in FIG. 21. The stratum corneum is exposed to the outside. The epidermis is located under the stratum corneum. The dermis is located under the epidermis. The stratum corneum includes keratinocyte and intercellular lipid, as shown in FIG. 22. The keratinocyte may include natural moisture factor. Intercellular lipids may include ceramides, fatty acids, cholesterol, etc. The moisture content of the stratum corneum may vary depending on the natural moisture factor.

Since the dielectric constant of water is greater than that of cholesterol, ceramide, etc., the higher the moisture content of the stratum corneum is, the greater the capacitance value of a person is, and vice versa. As such, as shown in FIG. 20, the capacitance value of a person increases with the skin moisture content of the person, and thus, the representative value $\Delta C_{ap}$ may be increased.

According to the illustrated exemplary embodiment shown in FIG. 20, the representative value $\Delta C_{ap}$ may be calculated based on the detection data DD in the first driving mode, and the moisture content of a person's skin may be calculated based on the representative value $\Delta C_{ap}$.

Figure 23:
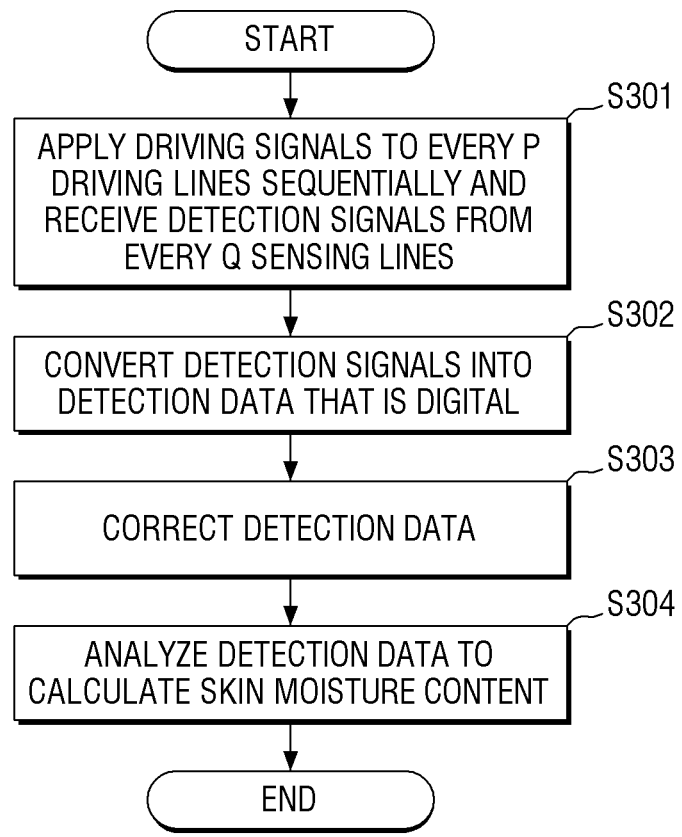
FIG. 23 is a flowchart for illustrating a touch sensing scheme by a sensor unit in a first driving mode according to an exemplary embodiment.

FIG. 23 is a flowchart for illustrating a touch sensing scheme by a sensor unit in a first driving mode according to an exemplary embodiment.

The touch sensing scheme illustrated in FIG. 23 is different from that shown in FIG. 16, in that step S303 is added. Since steps S301, S302, and S303 of FIG. 23 are substantially identical to steps S201, S202 and S203 of FIG. 16, and thus, repeated descriptions thereof will be omitted.

Figure 24:
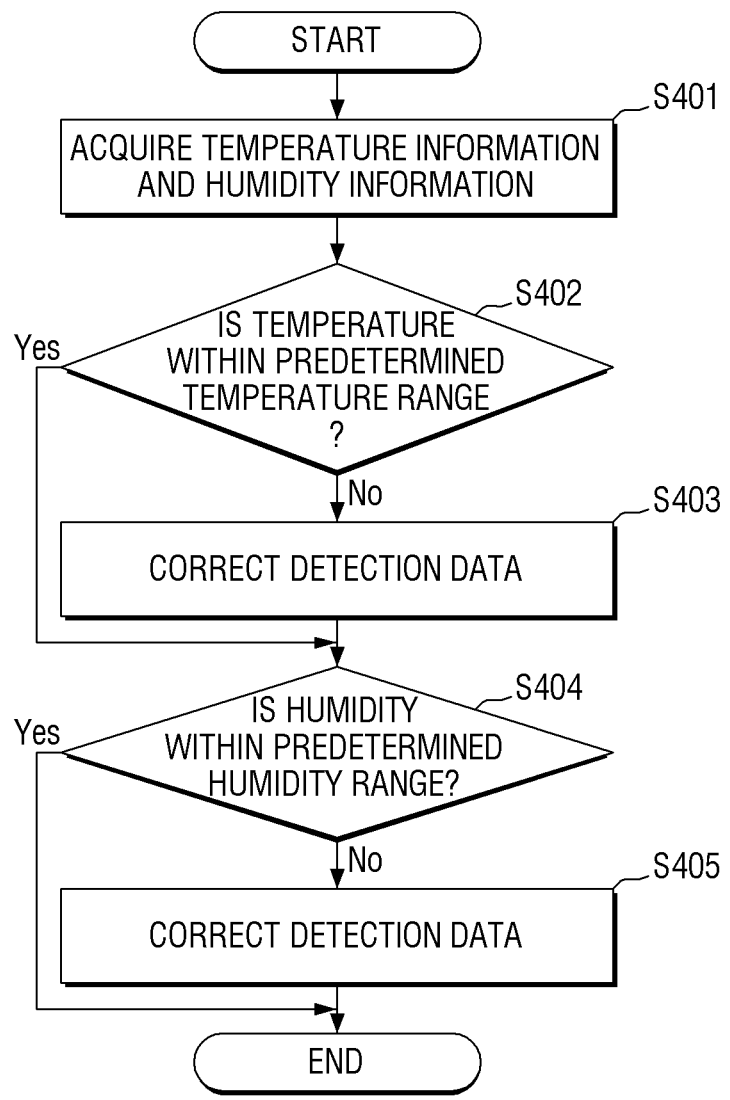
FIG. 24 is a flowchart illustrating step S303 of FIG. 23 according to an exemplary embodiment.
Figure 25:
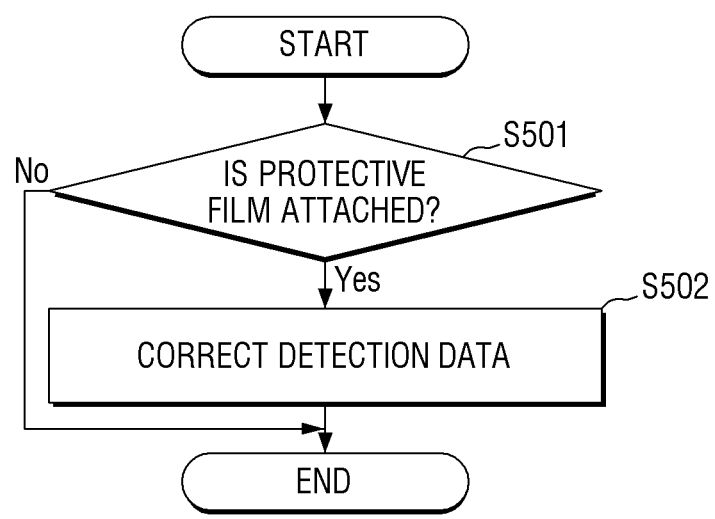
FIG. 25 is a flowchart illustrating step S303 of FIG. 23 according to another exemplary embodiment.
Figure 26:
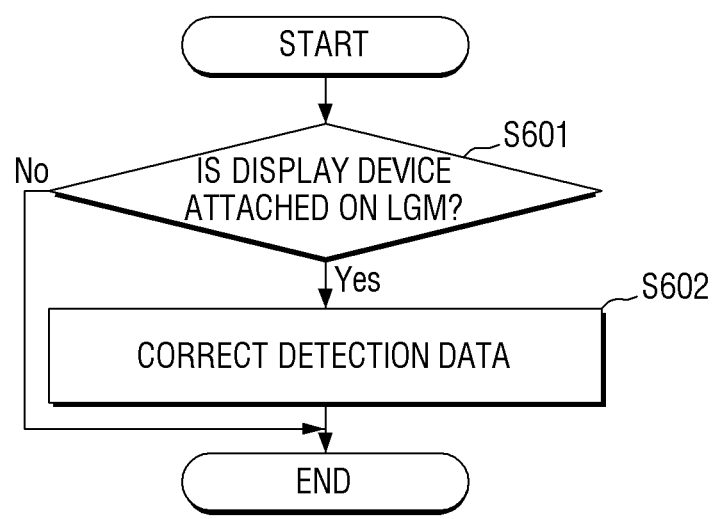
FIG. 26 is a flowchart illustrating step S303 of FIG. 23 according to still another exemplary embodiment.

Referring to FIG. 23, the main processor 710 may receive the detection data DD from the detector 332, and may determine the user's skin moisture by analyzing the detection data DD in the first driving mode. In doing so, after correcting the detection data DD according to the use environment of the display device 10 in step S303, the user may determine the user's skin moisture by analyzing the detection data DD. For example, the main processor 710 may correct the detection data DD in consideration of temperature and humidity, as shown in FIG. 24. Alternatively, the main processor 710 may correct the detection data DD based on whether there is a protective film, as illustrated in FIG. 25. Still alternatively, the main processor 710 may correct the detection data DD by determining whether the display device 10 is in contact with a ground mass, such as the ground and an object, as illustrated in FIG. 26.

FIG. 24 is a flowchart illustrating step S303 of FIG. 23 according to an exemplary embodiment.

Referring to FIG. 24, the main processor 710 may acquire temperature information and humidity information. For example, the temperature information and humidity information of the current location may be automatically transmitted from the Meteorological Agency through wireless communications with the Global Positioning System (GPS) when a skin moisture measurement application is run. Alternatively, the temperature information and humidity information of the current location may be manually input by the user when the skin moisture measurement application is run (step S401 in FIG. 24).

The main processor 710 then determines whether the temperature lies within a predetermined temperature range. For example, the predetermined temperature range may be about 5° C. to about 35° C., which is the room temperature. The main processor 710 corrects the sensed data DD when the temperature gets out of the predetermined temperature range. For example, when the temperature is lower than the lower limit of the predetermined temperature range, the detection data DD may be smaller than when the temperature is included in the predetermined temperature range, and thus, the main processor 710 may correct the detection data DD by incrementing it. In addition, when the temperature is lower than the upper limit of the predetermined temperature range, the detection data DD may be larger than when the temperature is included in the predetermined temperature range, and thus the main processor 710 may correct the detection data DD by reducing the detection data DD.

The main processor 710 may include a second look-up table that stores the corrected detection data based on the temperature and the detection data. The main processor 710 may correct the sensed data DD using the second look-up table (steps S402 and S403 of FIG. 24).

Then, the main processor 710 determines whether the temperature lies within a predetermined humidity range. For example, the predetermined humidity range may range from about 40% to about 60%. The main processor 710 corrects the detection data DD when the humidity is out of the predetermined humidity range. For example, when the humidity is lower than the lower limit of the predetermined humidity range, the detection data DD may be smaller than when the humidity is included in the predetermined humidity range, and thus, the main processor 710 may correct the detection data DD by increasing the detection data DD. In addition, when the humidity is lower than the upper limit of the predetermined humidity range, the detection data DD may be larger than when the humidity is included in the predetermined humidity range, and thus, the main processor 710 may correct the detection data DD by reducing the detection data DD.

The main processor 710 may include a third look-up table that stores the corrected detection data based on the humidity and the detection data. The main processor 710 may correct the detection data DD using the third look-up table (steps S404 and S405 of FIG. 24).

According to the illustrated exemplary embodiment shown in FIG. 24, a user's skin moisture can be more accurately determined by correcting the detection data DD based on the temperature and humidity according to the user's location.

FIG. 25 is a flowchart illustrating the step S303 of FIG. 23 according to another exemplary embodiment.

Referring to FIG. 25, the main processor 710 may acquire information on whether a protective film is attached to the cover window 100. For example, a user may manually input whether or not the protective film is attached when a skin moisture measurement application is run (step S501 of FIG. 25).

If the protective film is attached to the cover window 100, the main processor 710 corrects the detection data DD. For example, when the protective film is attached to the cover window 100, a user's the skin moisture is blocked by the protective film, and thus, the detection data DD may be smaller than that when the protective film is not attached. Therefore, the main processor 710 may correct the detection data DD by increasing the detection data DD when a protective film is attached on the cover window 100.

The main processor 710 may include a fourth look-up table that stores the corrected detection data associated with the detection data. The main processor 710 may correct the detection data DD using the fourth look-up table (step S502 of FIG. 25).

According to the illustrated exemplary embodiment shown in FIG. 25, a user's skin moisture can be more accurately determined by correcting the detection data DD based on whether a protective film is attached on the cover window 100.

FIG. 26 is a flowchart illustrating the step S303 of FIG. 23 according to another exemplary embodiment.

Referring to FIG. 26, the main processor 710 determines whether the display device 10 is in contact with a ground mass, such as the ground and an object. The main processor 710 may determine the inclination of the display device 10 and the rotation direction of the display device 10 based on the acceleration data from the acceleration sensor 740 and the angular velocity data from the gyro sensor 750. Therefore, the main processor 710 can determine whether the display device 10 is stationary based on the acceleration data and the angular velocity data. The main processor 710 may determine that the display device 10 is supported by a ground mass, such as the ground and an object, when the user measures skin moisture while the display device 10 is stationary (S601 in FIG. 26).

Then, when it is determined that the display device 10 is supported by a ground mass, such as the ground and an object, the main processor 710 corrects the detection data DD. For example, when it is determined that the display device 10 is supported by a ground mass, such as the ground and an object, the capacitances of the sensor electrodes are affected by the ground mass. Therefore, the detection data DD may be smaller than that when the display device 10 is not supported by the ground mass. As such, the main processor 710 may correct the detection data DD by increasing the detection data DD when a protective film is attached on the cover window 100.

The main processor 710 may include a fifth look-up table that stores the corrected detection data associated with the detection data. The main processor 710 may correct the detection data DD using the fifth look-up table (step S602 of FIG. 26).

According to the illustrated exemplary embodiment illustrated in FIG. 26, the user's skin moisture may be more accurately determined by correcting the detection data DD depending on whether the display device 10 is supported by a ground mass, such as the ground or an object.

In a sensor unit, a display device including the sensor unit, and a method for measuring moisture using the sensor unit constructed according to one or more exemplary embodiments, the number of mutual capacitances of the second unit sensor in the first driving mode may be greater than the number of mutual capacitances of the first unit sensor in the second driving mode, so that the capacitance of the mutual capacitances of the second unit sensor may be greater than the capacitance of mutual capacitances of the first unit sensor. In this manner, the difference between the amounts of change in mutual capacitances of the second unit sensors can become larger according to a person's skin moisture, so that the skin moisture can be measured more accurately.

In a sensor unit, a display device including the sensor unit, and a method for measuring moisture using the sensor unit constructed according to one or more exemplary embodiments, the frequency of the driving signal is controlled to be in a range from about 50 kHz to about 500 kHz, so that differences between the amounts of change in mutual capacitances of second unit sensors on a dry skin and the amounts of change in mutual capacitances of second unit sensors on a wet skin in a first driving mode can become larger. In this manner, a person's skin moisture may be measured more accurately.

In a sensor unit, a display device including the sensor unit, and a method for measuring moisture using the sensor unit constructed according to one or more exemplary embodiments, driving signals are applied sequentially to every P driving lines for approximately 1 to 1.5 seconds repeatedly in a first driving mode, so that differences between the amounts of change in mutual capacitances of second unit sensors on different person's skins can become larger. In this manner, a person's skin moisture may be measured more accurately.

In a sensor unit, a display device including the sensor unit, and a method for measuring moisture using the sensor unit constructed according to one or more exemplary embodiments, it is possible to more accurately determine a user's skin moisture by correcting the detection data based on the temperature and humidity according to the user's location.

In a sensor unit, a display device including the sensor unit, and a method for measuring moisture using the sensor unit constructed according to one or more exemplary embodiments, it is possible to determine more accurately a user's skin moisture by correcting the detection data based on whether a protective film is attached on a cover window.

In a sensor unit, a display device including the sensor unit, and a method for measuring moisture using the sensor unit constructed according to one or more exemplary embodiments, it is possible to determine more accurately a user's skin moisture by correcting the detection data based on whether a display device is supported by a ground mass such as the ground and an object.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A sensor unit comprising:
   a plurality of driving electrodes; and
   a plurality of sensing electrodes,
   wherein a first unit sensor is defined by R driving electrodes among the plurality of driving electrodes and S sensing electrodes among the plurality of sensing electrodes in a first driving mode,
   wherein a second unit sensor is defined by P driving electrodes among the plurality of driving electrodes and Q sensing electrodes among the plurality of sensing electrodes in a second driving mode,
   wherein P, Q, R and S are integers equal to or greater than 1,
   wherein R is smaller than P, and S is smaller than Q.

2. The sensor unit of claim 1, wherein a mutual capacitance of the second unit sensor is greater than a mutual capacitance of the first unit sensor.

3. The sensor unit of claim 1, wherein the first driving mode is for detecting a touch, and
   wherein the second driving mode is for calculating a skin moisture content.

4. The sensor unit of claim 1, further comprising:
   driving lines connected to the driving electrodes;
   sensing lines connected to the sensing electrodes;
   a driving signal output unit configured to apply driving signals to the driving lines; and
   a detector configured to receive detection signals from the sensing lines.

5. The sensor unit of claim 4, wherein the driving signal output unit is configured to sequentially apply the driving signals to every P driving lines in the second driving mode.

6. The sensor unit of claim 5, wherein the driving signal output unit is configured to simultaneously apply a same driving signal to the P driving lines in the second driving mode.

7. The sensor unit of claim 4, wherein the driving signal output unit is configured to sequentially apply the driving signals to every P driving lines for 1 to 1.5 seconds repeatedly in the second driving mode.

8. The sensor unit of claim 1, wherein a frequency of the driving signals in the first driving mode is same as a frequency of the driving signals in the second driving mode.

9. The sensor unit of claim 8, wherein a frequency of the driving signal is in a range of about 50 kHz to about 500 kHz in the second driving mode.

10. The sensor unit of claim 1, wherein a frequency of the driving signals in the first driving mode is smaller from a frequency of the driving signals in the second driving mode.

11. The sensor unit of claim 10, wherein a frequency of the driving signal is in a range of about 50 kHz to about 100 kHz in the second driving mode.

12. The sensor unit of claim 1, wherein a time period during which the driving signals are sequentially applied to every P driving lines in the second driving mode is longer than a time period during which the driving signals are sequentially applied to every R driving lines in the first driving mode.

13. The sensor unit of claim 4, wherein the detector is configured to convert the detection signals into digital detection data and output the digital detection data.

14. A display device comprising:
a display panel including:
   a display unit configured to display images; and
   a sensor unit configured to measure a skin moisture content, the sensor unit including a plurality of driving electrodes, and a plurality of sensing electrodes,
wherein a first unit sensor is defined by R driving electrodes among the plurality of driving electrodes and S sensing electrodes among the plurality of sensing electrodes in a first driving mode, and
wherein a second unit sensor is defined by P driving electrodes among the plurality of driving electrodes and Q sensing electrodes among the plurality of sensing electrodes in a second driving mode,
wherein P, Q, R and S are integers equal to or greater than 1, and
wherein R is smaller than P, and S is smaller than Q.

15. The sensor unit of claim 14, wherein a mutual capacitance of the second unit sensor is greater than a mutual capacitance of the first unit sensor.

16. The sensor unit of claim 14, further comprising:
driving lines connected to the driving electrodes;
sensing lines connected to the sensing electrodes;
a driving signal output unit configured to apply driving signals to the driving lines;
a detector configured to receive detection signals from the sensing lines and convert the detection signals into digital detection data; and
a main processor receives the digital detection data from the detector.

17. The sensor unit of claim 16, wherein the main processor is configured to calculate the skin moisture content based on the digital detection data.

18. The display device of claim 17, wherein the main processor is configured to correct the digital detection data when a temperature is not in a predetermined temperature range or a humidity is not in a predetermined humidity range.

19. The display device of claim 18, wherein:
corrected digital detection data has a greater value than the digital detection data when the temperature is lower than a lower limit of the predetermined temperature range; and
the corrected digital detection data has a lower value than the digital detection data when the temperature is higher than an upper limit of the predetermined temperature range.

20. The display device of claim 16, wherein the main processor is configured to increase the digital detection data when a protective film is disposed on the display panel or the display panel is determined as being stationary.

* * * * *